US006051385A

United States Patent [19]
Fuller et al.

[11] Patent Number: 6,051,385
[45] Date of Patent: Apr. 18, 2000

[54] COMPOSITIONS AND METHODS FOR IDENTIFYING AND TESTING THERAPEUTICS AGAINST HSV INFECTION

[75] Inventors: A. Oveta Fuller, Dexter; Qing-xue Li; Ning-hun C. McLaren, both of Ann Arbor; Aleida Perez, Howell, all of Mich.; Gangadharan Subramanian, Columbia, Md.

[73] Assignee: The Regents of the University of Michigan, Mich.

[21] Appl. No.: 08/955,531

[22] Filed: Oct. 22, 1997

[51] Int. Cl.$^7$ ............................. G01N 33/53; C12N 15/12
[52] U.S. Cl. ......................... 435/7.1; 435/7.2; 435/69.1; 435/252.3; 435/320.1; 536/23.5
[58] Field of Search ........................... 435/7.1, 7.2, 69.1, 435/252.3, 320.1; 536/23.5

[56] References Cited

U.S. PATENT DOCUMENTS

| | | | |
|---|---|---|---|
| 4,430,437 | 2/1984 | Hampar et al. | 436/548 |
| 4,642,333 | 2/1987 | Person | 530/350 |
| 4,661,349 | 4/1987 | Kino et al. | 424/89 |
| 4,683,195 | 7/1987 | Mullis et al. | 435/6 |
| 4,683,202 | 7/1987 | Mullis et al. | 435/91 |
| 4,704,362 | 11/1987 | Itakura et al. | 435/253 |
| 4,957,735 | 9/1990 | Huang | 424/85.8 |
| 4,965,188 | 10/1990 | Mullis et al. | 435/6 |
| 5,149,529 | 9/1992 | Ho et al. | 424/88 |
| 5,328,688 | 7/1994 | Roizman | 424/205.1 |
| 5,418,132 | 5/1995 | Olivo | 435/5 |
| 5,646,155 | 7/1997 | Wright | 514/261 |
| 5,652,096 | 7/1997 | Cimino | 435/6 |

FOREIGN PATENT DOCUMENTS

95/31544 11/1995 WIPO ............................ C12N 15/12

OTHER PUBLICATIONS

Montgomery et al. "Herpes Simplex Virus-1 Entry into Cells Mediated by a Novel Member of the TNF/NGF Receptor Family". Cell 87:427–436, Nov. 1996.

Morse et al., "Anatomy of Herpes Simplex Virus (HSV) DNA: X. Mapping of Viral Genes by Analysis of Polypeptides and Functions Specified by HSV–1 x HSV–2 Recombinants," *J. Virol.* 26:389–410 (1978).

Stevens et al., "Restriction of Herpes Simplex Virus By Macrophages," *J. Exp. Med.* 133:19–38 (1971).

Whitley, "Herpes Simplex Viruses," *Virology*, 2nd ed., Fields et. al., eds., Raven Press, N.Y., pp. 1843–1887 (1990).

Dundarov et al., "Immunotherapy With Inactivated Polyvalent Herpes Vaccines," *Dev. Biol. Standard* 52:351–57 (1982).

GRB Skinner et al., "Early Experience With <<Antigenoid>> Vaccine Ac NFU$_1$(S–) MRC Towards Prevention Or Modification Of Herpes Genitalis," *Dev. Biol. Standard* 52:333–44 (1982).

Chan, "Protective Immunization Of Mice With Specific HSV–1 Glycoproteins," *Immunol.* 49:343–52 (1983).

Stanberry et al., "Herpes Simplex Virus Glycoprotein Treatment of Recurrent Genital Herpes," *J. Infect. Dis.* 157:156–163 (1988).

Leib et al., "Immediate–Early Regulatory Gene Mutants Define Different Stages in the Establishment and Reactivation of Herpes Simplex Virus Latency," *J. Virol.* 63:759–768 (1989).

Shimeld et al., "Reactivation of Latent Infection and Induction of Recurrent Herpetic Eye Disease in Mice," *J. Gen. Virol.* 71:397–404 (1990).

Wigler et al., "Transformation of Mammalian Cells with an Amplifiable Dominant–Acting Gene," *Proc. Natl. Acad. Sci.* 77:3567–70 (1980).

Colbere–Garapin et al., A New Dominant Hybrid Selective Marker for Higher Eukaryotic Cells, *J. Mol. Biol.* 150:1–14 (1981).

Rhodes CA et al., "Transformation of Maize by Electroporation of Embryos," *Methods Mol. Biol.* 55:121–131 (1995).

Smith and Waterman, "Comparison of Biosequences," *Adv. Appl. Math.* 2:482–489 (1981).

Needleman and Wunsch, "A General Method Applicable to See the Search for Similarities in the Amino Acid Sequence of Two Proteins," *J. Mol. Biol.* 48: 443–453 (1970).

Pearson and Lipman, Improved Tools for Biological Sequence Comparison, *Proc. Natl. Acad. Sci. U.S.A.* 85:2444–2448 (1988).

Fuller and Spear, "Anti–Glycoprotein D Antibodies that Permit Adsorption But Block Infection By Herpes Simplex Virus 1 Prevent Virion–cell Fusion at the Cell Surface.," *Proc. Natl. Acad. Sci. USA.* 84:5454–5458 (1987).

DeLuca et al., "Isolation and Characterization of Deletion Mutants of Herpes Simplex Virus Type 1 in the Gene Encoding Immediate–Early Regulatory Protein ICP4," *J. Virol.* 56:558–570 (1985).

Wilson et al., "The Structure of an Antigenic Determinant in a Protein," *Cell* 37:767–778 (1984).

Zoller and Smith, "Oligonucleotide–directed Mutagenesis Using M13–Derived Vectors: An Efficient and General Procedure for the Production of Point Mutations In Any Fragment of DNA," *Nuc. Acids Res.* 10:6487–6500 (1982).

(List continued on next page.)

*Primary Examiner*—John Ulm
*Attorney, Agent, or Firm*—Medlen & Carroll, LLP

[57] ABSTRACT

The invention provides compositions a methods of identifying and testing therapeutics against HSV infection, and in particular, compositions comprising receptors which enable cell specific entry of HSV. The invention also provides a novel DNA sequence that encodes a protein B5T74 that confers the ability of herpes simplex virus (HSV) to infect and replicate in otherwise non-permissive cells. Also provided are vectors comprising the isolated nucleic acids encoding HSV receptors in host suitable for expression of the nucleic acids encoding the HSV receptors, fragments of the HSV receptors, or homologs of the HSV receptor. Further provided is a porcine cell system which expresses a herpes simplex virus receptor, but does not express endogenous, HSV entry receptors.

12 Claims, 14 Drawing Sheets

OTHER PUBLICATIONS

Harlow and Lane, Antibodies: A Laboratory Manual, Cold Spring Harbor Laboratory, Cold Spring Harbor, N.Y. (1988).

Kunkel et al., "Rapid and Efficient Site–Specific Mutagenesis Without Phenotypic Selection," *Methods Enzymol.* 154:367–382 (1987).

Sambrook et al., Molecular Cloning: A Laboratory Manual, 2nd Ed., Cold Spring Harbor Laboratory, Cold Spring Harbor, N.Y., (1989).

Ren et al., "Transgenic mice expressing a human poliovirus receptor: a new model for poliomyelitis," *Cell* 63:353–362 (1990).

Hogan, et al., in "Manipulating the Mouse Embryo: A Laboratory Manual," Cold Spring Harbor, N.Y.: Cold Spring Harbor Laboratory (1986).

Carter et al.,"High Level *Escherichia Coli* Expression and Production of a Bivalent Humanized Antibody Fragment," *Bio/Technology* 10:163–167 (1992).

Bebbington et al.,"High–Level Expression of a Recombinant Antibody from Myeloma Cells using a glutamin Synthetase Gene as an Amplifiable Selectable Marker," *Bio/Technology* 10:169–175 (1992).

Montgomery et al., "Herpes Simplex Virus–1 Entry into Cells Mediated by a Novel Member of the TNF/NGF Receptor Family," *Cell* 87:427–436 (1996).

Fuller, "Microbes and the Proteoglycan Connection," *J. Clin. Invest.* 93:460 (1994).

Fuller and Lee, "Herpes Simplex Virus Type 1 Entry through a Cascade of Virus–Cell Interactions Requires Different Roles of gD and gH in Penetration," *J. Virol.* 66:5002–5012 (1992).

Subramanian et al., "Swine Testis Cells Contain Functional Heparan Sulfate but Are Defective in Entry of Herpes Simplex Virus," *J. Virol.* 68:5667–5676 (1994).

Subramanian et al., "Defective entry of herpes simplex virus types 1 and 2 into porcine cells and lack of infection in infant pigs indicate species tropism," *J. Gen. Virol.* 76:2375–2379 (1995).

Marsters et al., "Herpesvirus Entry Mediator, a Member of the Tumor Necrosis Factor Receptor (TNFR) Family, Interacts with Members of the TNFR–associated Factor Family and Activates the Transcription Factors NF–κB and AP–1," *J. Biol. Chem.* 272:14029–14032 (1997).

Shieh et al., "Cell Surface Receptors for Herpes Simplex Virus Are Heparan Sulfate Proteoglycans," *J. Cell Biol.* 116:1273–1281 (1992).

FIG. 4

```
  1  CCTTCATACCGGCCCCTTCCCCCTCGGCTTTGCCTGGACAGCTCCTGCCCTCCCGCAGGGCCCACCTGTGTCCCC
 73  CAGCGCCGCTCCACCCAGCAGGCCTGAGCCCTGCCCTCTCTGCTGCCAGACACCCCTGCTGCCACTCTCCTGCT
145  GCTCGGGTTCTGAGGCACAGTTGTCACACAGCGGATTCTCTTCTCTTCTGGCCACACCCG
217  CAGCAATGGGCTGAGTTCCTCTGCTGCTGAGTTCATCCTGCTAGCTGGGTTCCCGAGCTGCCGGTCTGAGCCT
289  GAGGCATGGAGCCTCCTGGAGACTGGGGCCCTCCTCCCTGGAGATCCCAGAACCCAGAACCGACGTCTTGAGGC
  1                      M   E   P   P   G   D   W   G   P   P   P   W   R   S   T   P   R   T   D   V   L   R
361  TGGTGCTGTATCTCACCTTCCTGGGAGCCCCCTGCTACGCCCCAGCTCTGCCGTCCTGCAAGGAGGACGAGT
 23     L   V   L   Y   L   T   F   L   G   A   P   C   Y   A   P   A   L   P   S   C   K   E   D   E
433  ACCCAGTGGGCTCCCAGTGCTGCCCCAAGTGCAGTCCAGGTTATCGTGTGAAGGAGGCCTGCGGGGAGCTGA
 47     Y   P   V   G   S   E   C   C   P   K   C   S   P   G   Y   R   V   K   E   A   C   G   E   L
505  CGGGCACAGTGTGTGAACCCTGCCCTCCAGGACCTTGCCCACCTACATTGCCCACCTCAATGGCCTAAGCAAGTGTCTGC
 71     T   G   T   V   C   E   P   C   P   P   G   T   Y   I   A   H   L   N   G   L   S   K   C   L
577  AGTGCCAAATGTGTGACCCTGCCATGGGCCTGCGGGCCACGCGGAACTGCTCCAGGACAGAGAACGCCGTGT
 95     Q   C   Q   M   C   D   P   A   M   G   L   R   A   T   R   N   C   S   R   T   E   N   A   V
649  GTGGCTGCAGCCCAGGCCACTTCTGCATCGTCCAGGACGGGGACCACTGCGCGCCGTTACGCCA
119     C   G   C   S   P   G   H   F   C   I   V   Q   D   G   D   H   C   A   C   R   R   Y   A
721  CCTCCAGCCCGGGCCCAGAGGGCCAAGGCCACCGAGATCAGGAGGTCAGAACTGTGTCAGAACTGCCCCC
```

FIG. 4
CONTINUED

```
143   T  S  S  P  G  Q  R  V  Q  K  G  G  T  E  S  Q  D  T  L  C  Q  N  C  P
793   CGGGACCTTCTCTCCCAATGGGACCCTGGAGGAATGTCAGCAGCACCAAGTGCCAGTGCCTGGCTGGCTGTGACCA
167   P  G  T  F  S  P  N  G  T  L  E  E  C  Q  H  Q  T  K  C  S  W  L  V  T
865   AGGCCCGGAGCTGGGACCAGCAGCTCCCCACTGGGTATGGTGGTTTCTCTCAGGAGCCTCGTCATCGTCATTG
191   K  A  G  A  G  T  S  S  S  H  W  V  W  F  L  S  G  S  L  V  I  V  I
937   TTTGCTCCACAGTTGGCCTAATCATATGTGTGAAAAGAAGAAAGCCAAGGGTGATGTAGTCAAGGTGATCG
215   V  C  S  T  V  G  L  I  I  C  V  K  R  R  K  P  R  G  D  V  V  K  V  I
1009  TCTCCGTCCAGGCGGAAAAGACAGGAGGAGGCAGAAGGTGAGGCCCTGCAGGCCCACAGTCATTGAGGCCCCTCCGG
239   V  S  V  Q  R  K  R  Q  E  A  E  G  E  A  T  V  I  E  A  L  Q  A  P  P
1081  ACGTCACCACCGGTGCCCGTGGAGGAGACAATACCCTCATTCACGGGAGGAGCCCAAACCACTGACCCACAG
263   D  V  T  T  V  A  V  E  E  T  I  P  S  F  T  G  R  S  P  N  H  -
1153  ACTCTGCACCCCGACGGCCAGAGATACCTGGAGCGACGGCTGCTGAAAGAGGCTGTCCACCTGGGCAAACCAC
1225  CGGAGCCCGGAGGCTTGGGGCTGGCAGAGTCCCGGAGGCGCTCCCAGTGAGGGCGAGGTGGGGCC
1297  CCTGCTGGGTAGAGCTGGGACGCTGCCATTCCCACGTGCCAGTGAGGGCCTGGGCCTCTGTTCTG
1369  CTGTGGCCTGAGCTCCCAGAGTCCTGAGGAGCGCCAGCTGTCTGCCCTCACAGAGACCACACACCAGC
1441  CCTCCTGGGCCAGGGCCAGAGGGCCTCACAGGCCTTGGGACTGTGGGTTGGCTGACAGTGTTGTTAGTGGATACCA
1513  ACAGGCCCCGGGCACTGCCTCACAGCCTCTAAATTGGATTTCCGGTCCTGTCTTCTATTTGTCATGAAACAGTGTATTT
1585  CATCGGAAGTGATTTTCTAAATTGGATTTCCGGTCTTTTGTTTCTCCTCAAAAAAAAAAAAAAAAAAAA
1657  GGGGAGATGCTCTGTGGGACGATGTAAATATCTTCTTGTTCTCCTCAAAAAAAAAAAAAAAAAAAAAA
```

```
AAGCTTGGTACGNAGCTCGGATCCACTAGTAACGGCCGCCAGTGTGGTGGAATTCGTCCGCTGTGCCCGG       70
GCCTGCACCATGAGCCTCCCGGCCTTCATCGACATCAGTGAAGAAGATCAGCCTGCTGAGCTTCGTGCTT      140
ATCTGAAATCTAAAGGAGCTGAGATTTCAGAAGAGAACTCGGAAGGTGGACTTCATGTTGATTTAGCTCA      210
AATTATTGAAGCCTGTGATGTGTCTGAAGGAGGATGATAAAGATGTTGAAAGTGTGATGAACAGTGTG       280
GTATCCCTACTCTTGATCCTGGAACCAGACCAAGAAGCTTTGATTGATTGAAAGCCTATGTGAAAGCTGG      350
                   360       370       380       390       400       410       420
TCAAATTTCGCGAAGGTGAACGCCCGTCTCTGAGACTGCAGTGTTAAGCAACCTTTTCCACGGGATGGA      420
TAAGAATACTCCTGTAAGATACACAGTGTATTGCAGCCTTATTAAAGTGGCAGCATCTTGTGGGCCATC      490
CAGTACATCCCAACTGAGCTGGATCAAGTTAGAGGCACTTGTGGATTCTGACTGGAATCTCACCACTGAAAAAA   560
AGCACACCCTTTTAAGACTACTTTATGAGGACACTTGTGTGATTGTAAGAGAGTGATGCTGCTTCAAAACT     630
CATGGTGGAATTGCTCGGAAGTTACACAGAGGACAATGCTTCCCAGGCTCGAGTTGATGCCCACAGGTGT      700
                   710       720       730       740       750       760       770
ATTGTACGAGCATTGAAAGATCCAAATGCATTTCTTTTGACCACCTTCTTACTTTAAAACCAGTCAAGT      770
TTTGGAAGGCGAGCTTATTCATGATCTTTTAACCATTTTGTGAGTGCTAAATTGGCATCATATGTCAA      840
GTTTATCAGAATAATAAAGACTTCACTTGATTCACTTGGCCTGTTACATGAACAGAATATGGCAAAAATC     910
AGACTACTTACTTTTGGGAATGGCAGTAGAAAATAAGGAAATTTCTTTTGACACAATAAAATGGTCTACTGCAA  980
TTCAGATTGGAGCTGATGATGTTGAAGCATTGTTATTGACGCCGTAAGAACTAAAATGGTCTACTGCAA     1050
                    1060      1070      1080      1090      1100      1110      1120
AATTGATCAGACCCAGAGAAAAGTAGTTGTCAGTCATAGCACATCGGACATTTGGAAAACAGCAGTGG     1120
CAACAACTGTATGACACACTTAATGCCTGAAAACATCTGAACAAGTGAAAAACAGCCTTTGAGTC       1190
TTTCTGATACCTGAGTTTTTATGCTTATAATTTTGTTCTTTGAAAAAAAAGCCCTAAATCATAGTAAAA      1260
CATTATAAACTAAAAAAAAAAAAAAAAAAA 1288
```

FIG. 5

```
         10        20        30        40        50        60        70
         |         |         |         |         |         |         |
MSVPAFIDISEEDQAAELRAYLKSKGAEISEENSEGGLHVDLAQIIEACDVCLKEDDKDVESVMNSVVSL  70
LLILEPDKQEALIESLCEKLVKGRERPSLRLQLLSNLFHGMDKNTPVRYTVYCSLIKVAASCGAIQYI  140
PTELDQVRKWISDWNLTTEKKHTLLRLLYEALVDCKKSDAASKVMVELLGSYTEDNASQARVDAHRCIVR 210
ALKDPNAFLFDHLLTLKPVKFLEGELIHDLLTIFVSAKLASYVKFYQNNKDFIDSLGLLHEQNMAKMRLL 280
TFMGMAVENKEISFDTMQQELQIGADDVEAFVIDAVRTKMVYCKIDQTQRKVVVSHSTHRTFGKQQWQQL 350
         360       370       380       390       400       410       420
         |         |         |         |         |         |         |
YDTLNAWKQNLNKVKNSLLSLSDT  375
```

FIG. 6

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 1288 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO:1:

```
AAGCTTGGTA CGNAGCTCGG ATCCACTAGT AACGGCCGCC AGTGTGGTGG AATTCGTCCG      60

CTGTGCCCGG GCCTGCACCA TGAGCGTCCC GGCCTTCATC GACATCAGTG AAGAAGATCA     120

GGCTGCTGAG CTTCGTGCTT ATCTGAAATC TAAAGGAGCT GAGATTTCAG AAGAGAACTC     180

GGAAGGTGGA CTTCATGTTG ATTTAGCTCA AATTATTGAA GCCTGTGATG TGTGTCTGAA     240

GGAGGATGAT AAAGATGTTG AAAGTGTGAT GAACAGTGTG GTATCCCTAC TCTTGATCCT     300

GGAACCAGAC AAGCAAGAAG CTTTGATTGA AAGCCTATGT GAAAAGCTGG TCAAATTTCG     360

CGAAGGTGAA CGCCCGTCTC TGAGACTGCA GTTGTTAAGC AACCTTTTCC ACGGGATGGA     420

TAAGAATACT CCTGTAAGAT ACACAGTGTA TTGCAGCCTT ATTAAAGTGG CAGCATCTTG     480

TGGGGCCATC CAGTACATCC CAACTGAGCT GGATCAAGTT AGAAAATGGA TTTCTGACTG     540

GAATCTCACC ACTGAAAAAA AGCACACCCT TTTAAGACTA CTTTATGAGG CACTTGTGGA     600

TTGTAAGAAG AGTGATGCTG CTTCAAAAGT CATGGTGGAA TTGCTCGGAA GTTACACAGA     660

GGACAATGCT TCCCAGGCTC GAGTTGATGC CCACAGGTGT ATTGTACGAG CATTGAAAGA     720

TCCAAATGCA TTTCTTTTTG ACCACCTTCT TACTTTAAAA CCAGTCAAGT TTTTGGAAGG     780

CGAGCTTATT CATGATCTTT TAACCATTTT TGTGAGTGCT AAATTGGCAT CATATGTCAA     840

GTTTTATCAG AATAATAAAG ACTTCATTGA TTCACTTGGC CTGTTACATG AACAGAATAT     900

GGCAAAAATG AGACTACTTA CTTTTATGGG AATGGCAGTA GAAAATAAGG AAATTTCTTT     960

TGACACAATG CAGCAAGAAC TTCAGATTGG AGCTGATGAT GTTGAAGCAT TTGTTATTGA    1020

CGCCGTAAGA ACTAAAATGG TCTACTGCAA AATTGATCAG ACCCAGAGAA AAGTAGTTGT    1080

CAGTCATAGC ACACATCGGA CATTTGGAAA ACAGCAGTGG CAACAACTGT ATGACACACT    1140

TAATGCCTGG AAACAAAATC TGAACAAAGT GAAAACAGC CTTTTGAGTC TTTCTGATAC    1200

CTGAGTTTTT ATGCTTATAA TTTTTGTTCT TGAAAAAAA AGCCCTAAAT CATAGTAAAA    1260

CATTATAAAC TAAAAAAAAA AAAAAAA                                       1288
```

-continued (2) INFORMATION FOR SEQ ID NO:2:

(i) SEQUENCE CHARACTERISTICS:
        (A) LENGTH: 374 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:2:

```
Met Ser Val Pro Ala Phe Ile Asp Ile Ser Glu Glu Asp Gln Ala Ala
1               5                   10                  15

Glu Leu Arg Ala Tyr Leu Lys Ser Lys Gly Ala Glu Ile Ser Glu Glu
            20                  25                  30

Asn Ser Glu Gly Gly Leu His Val Asp Leu Ala Gln Ile Ile Glu Ala
        35                  40                  45

Cys Asp Val Cys Leu Lys Glu Asp Lys Asp Val Glu Ser Val Met
    50                  55                  60

Asn Ser Val Val Ser Leu Leu Ile Leu Glu Pro Asp Lys Gln Glu
65                  70                  75                  80

Ala Leu Ile Glu Ser Leu Cys Glu Lys Leu Val Lys Phe Arg Glu Gly
                85                  90                  95

Glu Arg Pro Ser Leu Arg Leu Gln Leu Leu Ser Asn Leu Phe His Gly
            100                 105                 110

Met Asp Lys Asn Thr Pro Val Arg Tyr Thr Val Tyr Cys Ser Leu Ile
        115                 120                 125

Lys Val Ala Ala Ser Cys Gly Ala Ile Gln Tyr Ile Pro Thr Glu Leu
    130                 135                 140

Asp Gln Val Arg Lys Trp Ile Ser Asp Trp Asn Leu Thr Thr Glu Lys
145                 150                 155                 160

Lys His Thr Leu Leu Arg Leu Leu Tyr Glu Ala Leu Val Asp Cys Lys
                165                 170                 175

Lys Ser Asp Ala Ala Ser Lys Val Met Val Glu Leu Leu Gly Ser Tyr
            180                 185                 190

Thr Glu Asp Asn Ala Ser Gln Ala Arg Val Asp Ala His Arg Cys Ile
        195                 200                 205

Val Arg Ala Leu Lys Asp Pro Asn Ala Phe Leu Phe Asp His Leu Leu
    210                 215                 220

Thr Leu Lys Pro Val Lys Phe Leu Glu Gly Glu Leu Ile His Asp Leu
225                 230                 235                 240

Leu Thr Ile Phe Val Ser Ala Lys Leu Ala Ser Tyr Val Lys Phe Tyr
                245                 250                 255

Gln Asn Asn Lys Asp Phe Ile Asp Ser Leu Gly Leu Leu His Glu Gln
            260                 265                 270

Asn Met Ala Lys Met Arg Leu Leu Thr Phe Met Gly Met Ala Val Glu
        275                 280                 285

Asn Lys Glu Ile Ser Phe Asp Thr Met Gln Gln Glu Leu Gln Ile Gly
    290                 295                 300

Ala Asp Asp Val Glu Ala Phe Val Ile Asp Ala Val Arg Thr Lys Met
305                 310                 315                 320

Val Tyr Cys Lys Ile Asp Gln Thr Gln Arg Lys Val Val Ser His
                325                 330                 335

Ser Thr His Arg Thr Phe Gly Lys Gln Gln Trp Gln Gln Leu Tyr Asp
            340                 345                 350

Thr Leu Asn Ala Trp Lys Gln Asn Leu Asn Lys Val Lys Asn Ser Leu
```

Leu Ser Leu Ser Asp Thr
370

(2) INFORMATION FOR SEQ ID NO:3:

(i) SEQUENCE CHARACTERISTICS:
        (A) LENGTH: 1724 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

```
CCTTCATACC GGCCCTTCCC CTCGGCTTTG CCTGGACAGC TCCTGCCTCC CGCAGGGCCC      60
ACCTGTGTCC CCCAGCGCCG CTCCACCCAG CAGGCCTGAG CCCCTCTCTG CTGCCAGACA     120
CCCCCTGCTG CCCACTCTCC TGCTGCTCGG GTTCTGAGGC ACAGCTTGTC ACACCGAGGC     180
GGATTCTCTT TCTCTTTCTC TTCTGGCCCA CAGCCGCAGC AATGGCGCTG AGTTCCTCTG     240
CTGGAGTTCA TCCTGCTAGC TGGGTTCCCG AGCTGCCGGT CTGAGCCTGA GGCATGGAGC     300
CTCCTGGAGA CTGGGGGCCT CCTCCCTGGA GATCCACCCC CAGAACCGAC GTCTTGAGGC     360
TGGTGCTGTA TCTCACCTTC CTGGGAGCCC CCTGCTACGC CCCAGCTCTG CCGTCCTGCA     420
AGGAGGACGA GTACCCAGTG GGCTCCGAGT GCTGCCCCAA GTGCAGTCCA GGTTATCGTG     480
TGAAGGAGGC CTGCGGGGAG CTGACGGGCA CAGTGTGTGA ACCCTGCCCT CCAGGCACCT     540
ACATTGCCCA CCTCAATGGC CTAAGCAAGT GTCTGCAGTG CCAAATGTGT GACCCAGCCA     600
TGGGCCTGCG CGCGACGCGG AACTGCTCCA GGACAGAGAA CGCCGTGTGT GGCTGCAGCC     660
CAGGCCACTT CTGCATCGTC CAGGACGGGG ACCACTGCGC CGCGTGCCGC CGTTACGCCA     720
CCTCCAGCCC GGGCCAGAGG GTGCAGAAGG GAGGCACCGA GAGTCAGGAC ACCCTGTGTC     780
AGAACTGCCC CCCGGGGACC TTCTCTCCCA ATGGGACCCT GGAGGAATGT CAGCACCAGA     840
CCAAGTGCAG CTGGCTGGTG ACGAAGGCCG GAGCTGGGAC CAGCAGCTCC CACTGGGTAT     900
GGTGGTTTCT CTCAGGGAGC CTCGTCATCG TCATTGTTTG CTCCACAGTT GGCCTAATCA     960
TATGTGTGAA AAGAAGAAAG CCAAGGGGTG ATGTAGTCAA GGTGATCGTC TCCGTCCAGC    1020
GGAAAAGACA GGAGGCAGAA GGTGAGGCCA CAGTCATTGA GGCCCTGCAG GCCCCTCCGG    1080
ACGTCACCAC GGTGGCCGTG GAGGAGACAA TACCCTCATT CACGGGGAGG AGCCCAAACC    1140
ACTGACCCAC AGACTCTGCA CCCCGACGCC AGAGATACCT GGAGCGACGG CTGCTGAAAG    1200
AGGCTGTCCA CCTGGCGAAA CCACCGGAGC CCGGAGGCTT GGGGGCTCCG CCCTGGGCTG    1260
GCTTCCGTCT CCTCCAGTGG AGGGAGAGGT GGGGCCCCTG CTGGGGTAGA GCTGGGGACG    1320
CCACGTGCCA TTCCCATGGG CCAGTGAGGG CCTGGGGCCT CTGTTCTGCT GTGGCCTGAG    1380
CTCCCCAGAG TCCTGAGGAG GAGCGCCAGT TGCCCCTCGC TCACAGACCA CACACCCAGC    1440
CCTCCTGGGC CAGCCCAGAG GGCCCTTCAG ACCCCAGCTG TCTGCGCGTC TGACTCTTGT    1500
GGCCTCAGCA GGACAGGCCC CGGGCACTGC CTCACAGCCA AGGCTGGACT GGGTTGGCTG    1560
CAGTGTGGTG TTTAGTGGAT ACCACATCGG AAGTGATTTT CTAAATTGGA TTTGAATTCC    1620
GGTCCTGTCT TCTATTTGTC ATGAAACAGT GTATTTGGGG AGATGCTGTG GGAGGATGTA    1680
AATATCTTGT TTCTCCTCAA AAAAAAAAAA AAAAAAAAA AAAA                      1724
```

(2) INFORMATION FOR SEQ ID NO:4:

(i) SEQUENCE CHARACTERISTICS:
    (A) LENGTH: 283 amino acids
    (B) TYPE: amino acid
    (C) STRANDEDNESS: Not Relevant
    (D) TOPOLOGY: linear (ii) MOLECULE TYPE: protein (xi) SEQUENCE DESCRIPTION: SEQ ID NO:4:

```
Met Glu Pro Pro Gly Asp Trp Gly Pro Pro Trp Arg Ser Thr Pro
  1               5                  10                  15

Arg Thr Asp Val Leu Arg Leu Val Leu Tyr Leu Thr Phe Leu Gly Ala
             20                  25                  30

Pro Cys Tyr Ala Pro Ala Leu Pro Ser Cys Lys Glu Asp Glu Tyr Pro
         35                  40                  45

Val Gly Ser Glu Cys Cys Pro Lys Cys Ser Pro Gly Tyr Arg Val Lys
 50                  55                  60

Glu Ala Cys Gly Glu Leu Thr Gly Thr Val Cys Glu Pro Cys Pro Pro
 65                  70                  75                  80

Gly Thr Tyr Ile Ala His Leu Asn Gly Leu Ser Lys Cys Leu Gln Cys
                 85                  90                  95

Gln Met Cys Asp Pro Ala Met Gly Leu Arg Ala Thr Arg Asn Cys Ser
             100                 105                 110

Arg Thr Glu Asn Ala Val Cys Gly Cys Ser Pro Gly His Phe Cys Ile
         115                 120                 125

Val Gln Asp Gly Asp His Cys Ala Ala Cys Arg Arg Tyr Ala Thr Ser
130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala
             180                 185                 190

Gly Ala Gly Thr Ser Ser Ser His Trp Val Trp Trp Phe Leu Ser Gly
         195                 200                 205

Ser Leu Val Ile Val Ile Val Cys Ser Thr Val Gly Leu Ile Ile Cys
210                 215                 220

Val Lys Arg Arg Lys Pro Arg Gly Asp Val Val Lys Val Ile Val Ser
225                 230                 235                 240

Val Gln Arg Lys Arg Gln Glu Ala Glu Gly Glu Ala Thr Val Ile Glu
                245                 250                 255

Ala Leu Gln Ala Pro Pro Asp Val Thr Thr Val Ala Val Glu Glu Thr
             260                 265                 270

Ile Pro Ser Phe Thr Gly Arg Ser Pro Asn His
         275                 280
```

(2) INFORMATION FOR SEQ ID NO:5:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:5:

```
Glu Phe Tyr Pro Tyr Asp Val Pro Asp Tyr Ala Ser Leu
  1               5                  10
```

(2) INFORMATION FOR SEQ ID NO:6:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

ACAAGACCGT GC                                      12

COMPOSITIONS AND METHODS FOR IDENTIFYING AND TESTING THERAPEUTICS AGAINST HSV INFECTION

This invention was made with government support awarded by NIAID. The government has certain rights in the invention.

FIELD OF THE INVENTION

The invention generally relates to compositions and methods for identifying and testing therapeutics against HSV infection, and in particular, compositions comprising receptors which enable cell specific entry of HSV.

BACKGROUND OF THE INVENTION

The herpes viruses include the herpes simplex viruses (HSV), comprising two closely related variants designated types 1 (HSV-1) and 2 (HSV-2). These types are related immunologically, but most of their proteins carry distinguishing characteristics which allow them to be differentiated (See Morse et al., *J Virol.*, 26(2), 389–410, 1978). The herpes simplex virus is a double stranded DNA virus having a genome of about 150 to 160 Kb, packaged within an icosahedral nucleocapsid, enveloped in a membrane. The membrane includes a number of virus-specific glycoproteins, the most abundant of which are gB, gC, gD, and gE. The proteins gB and gD are cross-reactive between IISV-1 and HSV-2.

HSV-1 and HSV-2 are responsible for a variety of human diseases, such as skin infection, oral and genital herpes, viral encephalitis, and the like. Infections in humans are characterized by episodes of epithelial eruptions involving active virus production alternating without clinical symptoms. The virus persists to cause recurrent disease and establishes both lytic and latent infections in the central nervous system (CNS) of its host, specifically the neural ganglia [See Stevens et al., *J Exp. Med.*, 133:19 (1971)]. This tropism for the CNS may result in encephalitis [See Whitley, *Virology*, 2nd ed., Fields et. al., eds., Raven Press, N.Y. 1843–1887 (1990)]. Oral herpes (cold sores and fever blisters) is prevalent and is an inconvenience for approximately 60% of the population of industrial countries, whereas genital herpes is a major cause of sexually transmitted genital herpes which is in epidemic proportions in some populations. Infection with HSV can also cause more serious infections, the most serious of which are sight-threatening keratitis and life-threatening encephalitis. Also, herpesviruses have become increasingly important causes of human morbidity and mortality, especially in intensive care units for immunocompromised or immunosuppressed patients. Furthermore, HSV related disease in immunocompromised individuals such as newborns, leukemia patients, organ transplant recipients and AIDS patients has become an increasingly prevalent and difficult problem.

Several HSV vaccines have been prepared. S. Dundarov et al., *Dev Biol Standard*, 52:351–57 (1982) describes the treatment of humans with formalin-inactivated HSV in distilled water. GRB Skinner et al., *Dev Biol Standard*, 52:333–44 (1982) describes the treatment of humans with formalin-inactivated HSV in saline. L. Chan, *Immunol*, 49:343–52 (1983) describes the protective immunization of mice against HSV challenge by vaccination with gD in saline. Kino et al., U.S. Pat. No. 4,661,349 describes vaccines comprising purified HSV gB with alum. Person, U.S. Pat. No. 4,642,333 describes HSV gB and its administration to rabbits in Freund's adjuvant. L. R. Stanberry et al., *J Infect Dis*, 157:156–163 (1988) reports the use of rgD and rgB in a vaccine to ameliorate the symptoms of genital herpes infection in guinea pigs. Ho et al., reports the liposomal formulations of recombinant Herpes virus surface glycoprotein D-1 (HSV rgD-1) in the treatment and prevention of HSV disease (U.S. Pat. No. 5,149,529 incorporated herein by reference).

Presently, much of the antiviral research focuses on providing drugs with (i) improved oral bioavailability and pharmacokinetics which permit less frequent oral or topical dosing for suppressive treatment of herpes simplex virus (HSV) infections, (ii) different mechanisms of action for synergic effects in treating resistant HSV infections in the immunocompromised host and (iii) improved efficacy. Current strategies include developing antiviral agents that target enzymes or (viral factors essential for infection) or will inhibit other steps in the viral infection cycle, such as protein synthesis, capsid assembly or virus spread. In this regard, the viral DNA polymerase has been an important target for nucleoside analogs such as acyclovir, bromovinyl-deoxyuridine and Dihydroxy-phenylguanines (DHPG). However, lately, the severity of disease and the frequency of acyclovir resistance has increased in immunocompromised patients.

Currently, the in vitro and in vivo screens or methods used for identifying molecules that specifically impart HSV infection include a murine in vitro explant-cocultivation model [See Leib et al.,*J Virol.* 63: 759 (1989)], a murine eye model [See Shimeld et al., *J Gen. Virol.* 71:397 (1990)], and other animal models (See U.S. Pat. No. 5,646,155, incorporated herein by reference). Some of these have limited specificity, and/or are time-consuming and/or are labor intensive. Thus, methods are needed for high throughput screening of antiviral therapeutics against HSV infections, that provides rapid compound discovery in a cost efficient manner.

SUMMARY OF THE INVENTION

The invention generally relates to compositions and methods for identifying and testing compounds against HSV infection, and in particular, compositions comprising receptors which enable cell specific entry of HSV. In preferred embodiments, these receptors are useful for identifying compounds that will inhibit HSV uptake and replication.

It is not intended that the present invention be limited to particular HSV receptors. A variety of closely related vertebrate homologues of HSV receptors are contemplated that are involved in the uptake and subsequent replication of the herpes simplex virus. In one embodiment, the present invention contemplates a composition, comprising an isolated nucleic acid encoding a human herpes simplex virus receptor or portion thereof, said receptor comprising the polypeptide set forth in SEQ ID NO: 2. While it is not intended that the present invention be limited to a particular nucleic acid sequence, in one embodiment, said nucleic acid comprises at least a portion of the sequence set forth in SEQ ID NO: 1. It is preferred that said nucleic acid is in a vector and vector is in a host cell. While human host cells are contemplated, non-human cells are preferred, such as porcine cells, since a variety of porcine cells do not express an endogenous human herpes simplex virus receptor.

The receptors contemplated by the present invention have the biological activity of transforming cells previously non-permissive for herpes simplex virus infection into cells permissive for herpes simplex virus infection. Purified polypeptides comprising all or part of the HSV receptor are also provided by the present invention. These polypeptides can be utilized to diagnose infection, to treat infection, as well as prevent infection by herpes simplex virus. Polypeptides of the present invention can be expressed in a transformed cell and utilized to test the efficacy of compounds in anti-HSV infectivity assays.

In this regard, the present invention contemplates a method for testing compounds, comprising: a) providing: i) human herpes simplex virus, ii) a first population of cells, said first population being non-permissive for human herpes simplex virus, iii) an isolated nucleic acid encoding a human herpes simplex virus receptor or portion thereof, and iv) a compound suspected of being capable of inhibiting human herpes simplex virus entry into cells; b) transfecting said first population of cells with said nucleic acid under conditions so as to create a second population of cells being permissive for human herpes simplex virus; c) mixing, in any order, said human herpes simplex virus, said compounds amd said second population of cells; and d) measuring the extent of human herpes simplex virus entry to said cells.

While not limited in such methods to particular nucleic acids, in one embodiment, said nucleic acid comprises at least a portion of the sequence set forth in SEQ ID NO: 1. In another embodiment, said nucleic acid comprises at least a portion of the sequence set forth in SEQ ID NO: 3.

The present invention contemplates screening libraries of compounds in this manner. Such compounds tested may include antibodies, and more specifically, antibodies suspected of being capable of inhibiting human herpes simplex virus entry into cells (such as antibodies directed to receptors).

The present invention also provides an isolated nucleic acid molecule, comprising a nucleic acid encoding a polypeptide having the biological activity of a HSV receptor. An isolated nucleic acid that hybridizes with the HSV receptor-encoding nucleic acid under specified stringency conditions is also provided. The isolated nucleic acid of the present invention can be utilized to express the herpes simplex virus receptor, or active fragments thereof, and to diagnose infection by HSV.

The present invention also provides vectors comprising the isolated nucleic acids encoding a HSV receptor or fragments thereof. These vectors can be utilized for expression of the nucleic acids in host expression systems to produce the entire HSV receptor, fragments of the receptor, including functional domains of the receptor.

The present invention contemplates compound screening using a variety of assay formats. In one embodiment, the present invention contemplates a method for compound screening, comprising: a) providing: i) herpes simplex virus, ii) a first population of cells, said first population permissive to HSV (e.g., having one or more receptors capable of binding to herpes simplex virus), iii) a second population of cells, said second population non-permissive to HSV (e.g., lacking receptors capable of binding to herpes simplex virus), and iv) one or more compounds for screening; b) mixing, in any order, said herpes simplex virus and said one or more compounds with i) said first population of cells, and ii) said second population of cells, and c) measuring the extent of herpes simplex virus binding to said cells.

It is not intended that the present invention be limited to the nature of the cells having or lacking receptors capable of binding to said herpes simplex virus. In one embodiment, the clonal cells are used (i.e. cells derived from a single cell). In a particular embodiment, clonal cells are selected from the group consisting of several clones of swine kidney cells, transformed swine cells from other tissues or primary porcine cells. In other embodiments, clonal cells are selected from Chinese hamster ovary (CHO) cells, Xenopus oocytes, or GroC mouse L cells.

The present invention specifically contemplates using nucleic acids to transfect non-permissive cells, thereby making them permissive to HSV infection. In one embodiment, non-permissive cells are transfected with nucleic acid encoding a receptor for HSV. Said receptor confers the ability of said cells to be infected. In other words, without said receptor, said cells are lacking any receptor that permits viral entry and subsequent infection.

Further provided by the present invention is a clonal non-permissive porcine cell line which on transfection with nucleic acids encoding receptors of the present invention, expresses a herpes simplex virus receptor, but does not express an endogenous, active HSV receptor. In other embodiments, the porcine cell line, on transfection, expresses one or more receptors which enable HSV entry and replication. The present invention also comprises using the porcine cell line, as a test model for testing the efficacy of HSV vaccines, as well as other therapies designed to prevent infection and treat infection by herpes simplex virus.

The present invention contemplates using the polynucleotides of the present invention for expression of the polypeptides in vitro and in vivo. Therefore, the present invention contemplates the polynucleotide sequence of SEQ ID NO:1 as well as fragments and variants thereof, wherein said polynucleotide sequence is contained on a recombinant expression vector. It is also contemplated that such vectors will be introduced into a variety of host cells, both eukaryotic and prokaryotic (e.g., bacteria such as *E. coli*).

In one embodiment, the vector further comprises a promoter. It is not intended that the present invention be limited to a particular promoter. Any promoter sequence which is capable of directing expression of an operably linked nucleic acid sequence encoding a portion of the HSV receptor (or other HSV receptor polypeptides of interest as described above) is contemplated to be within the scope of the invention. Promoters include, but are not limited to, promoter sequences of bacterial and viral origins. Promoters of bacterial origin include, but are not limited to SP6 AND T7. Viral promoters include, but are not limited to CMV IE, Rous sarcoma virus (RSV) long terminal repeat (LTR), SV40 promoter and enhancer (large T Antigen).

The invention is not limited to the number of promoters used to control expression of a nucleic acid sequence of interest. Any number of promoters may be used so long as expression of the nucleic acid sequence of interest is controlled in a desired manner.

The promoter activity of any nucleic acid sequence in host cells may be determined (i.e., measured or assessed) using methods well known in the art and exemplified herein. For example, a candidate promoter sequence may be tested by ligating it in-frame to a reporter gene sequence to generate a reporter construct, introducing the reporter construct into host cells (e.g., primary or clonal porcine cells) using methods described herein, and detecting the expression of the reporter gene (e.g., detecting the presence of encoded mRNA or encoded protein, or the activity of a protein encoded by the reporter gene). The reporter gene may confer antibiotic resistance. Examples of reporter genes include, but are not limited to, zeo which confers resistance to zeocin, dhfr which confers resistance to methotrexate [Wigler M et al., (1980) *Proc Natl Acad Sci* 77:3567–70]; npt, which confers resistance to the aminoglycosides neomycin and G-418 [Colbere-Garapin F et al., (1981) *J. Mol. Biol.*

150:1–14] and pat, which confer resistance to phosphinotricin acetyl transferase. Recently, the use of a reporter gene system which expresses visible markers that can be detected by auto-fluorescence (i.e., Green Fluorescent Protein [GFP]) has gained popularity. These markers and others that can be detected by histochemical staining such as β-glucuronidase and its substrate (X-Gluc), luciferase and its substrate (luciferin), and β-galactosidase and its substrate (X-Gal) are being widely used not only to identify transformants, but also to quantify the amount of transient or stable protein expression attributable to a specific vector system [Rhodes CA et al. (1995) *Methods Mol Biol* 55:121–131].

In addition to a promoter sequence, the expression construct preferably contains a transcription termination sequence downstream of the nucleic acid sequence of interest to provide for efficient termination. The termination sequences of the expression constructs are not critical to the invention. The termination sequence may be obtained from the same gene as the promoter sequence or may be obtained from different genes.

If the mRNA encoded by the nucleic acid sequence of interest is to be efficiently translated, polyadenylation sequences are also commonly added to the expression construct. Examples of the polyadenylation sequences include, but are not limited to, SV40 poly A, adenovirus poly A, bovine growth hormone (BGH) poly A.

The invention is not limited to constructs which express a single nucleic acid sequence of interest. Constructs which contain a plurality of (i.e., two or more) nucleic acid sequences under the transcriptional control of the same promoter sequence are expressly contemplated to be within the scope of the invention. Also included within the scope of this invention are constructs which contain the same or different nucleic acid sequences under the transcriptional control of different promoters. Such constructs may be desirable to, for example, target expression of the same or different nucleic acid sequences of interest to selected porcine cell systems.

As noted above, the present invention contemplates using the polynucleotides of the present invention for expression of a portion of HSV receptor polypeptides in vitro and in vivo. Where expression takes place in vivo, the present invention contemplates transgenic animals. The transgenic animals of the invention are not limited to animals in which each and every cell expresses the nucleic acid sequence of interest. Included within the scope of this invention is any animal (e.g., mouse, pig, etc.) which contains at least one cell which expresses the nucleic acid sequence of interest. It is preferred, though not necessary, that the transgenic animal express the nucleic acid sequence of interest in more than one cell, and more preferably in one or more tissue.

The fact that transformation of cells has taken place with the nucleic acid sequence of interest may be determined using any number of methods known in the art. Such methods include, but are not limited to, restriction mapping of genomic DNA, PCR analysis, DNA-DNA hybridization, DNA-RNA hybridization, and DNA sequence analysis.

Expressed polypeptides (or fragments thereof) can be immobilized (covalently or non-covalently) on solid supports or resins for use in isolating HSV-binding molecules. Such polypeptides can also be used to make antibodies.

It is not necessary that the present invention utilize complete HSV particles. Incomplete HSV particles are also contemplated, provided that they either a) bind to the above-described receptors and/or b) enter the cells and/or c) cause the cells to be infected.

The present invention also contemplates using defective and/or non-infectious HSV. Specifically, the present invention contemplates using HSV variants or mutants that, while capable of interacting with the receptors of the present invention, are non-infectious.

DESCRIPTION OF THE FIGURES

FIG. 4 shows both the nucleotide sequence (SEQ ID NO:3) and amino acid sequence (SEQ ID NO:4) of the human herpes simplex virus receptor, HVEM.

FIG. 5 shows the nucleotide sequence of (SEQ ID NO:1) the cDNA in the isolated B5T74 clone.

FIG. 6 shows the amino acid composition (SEQ ID NO:2) of the protein expressed from the B5T74 clone.

FIG. 9 represents an analysis of B5 relatedness to HVEM or TNFR family members.

FIG. 12A shows a representative SDS-PAGE of immunoprecipitated proteins from radiolabeled cells. The left lanes are immunoprecipitated with anti-gD monoclonal antibody, while the right panel with anti-HVEM polyclonal antibody.

FIG. 12B shows representative Western blots of IP lysates. Panel A :gD immunoprecipitant probed with anti-gD in Western. Panel B is anti-HVEM IP probed in Western with anti-gD. Panels C and D were probed in Westerns by an anti-gH monoclonal antibody.

DEFINITIONS

Figure 1:
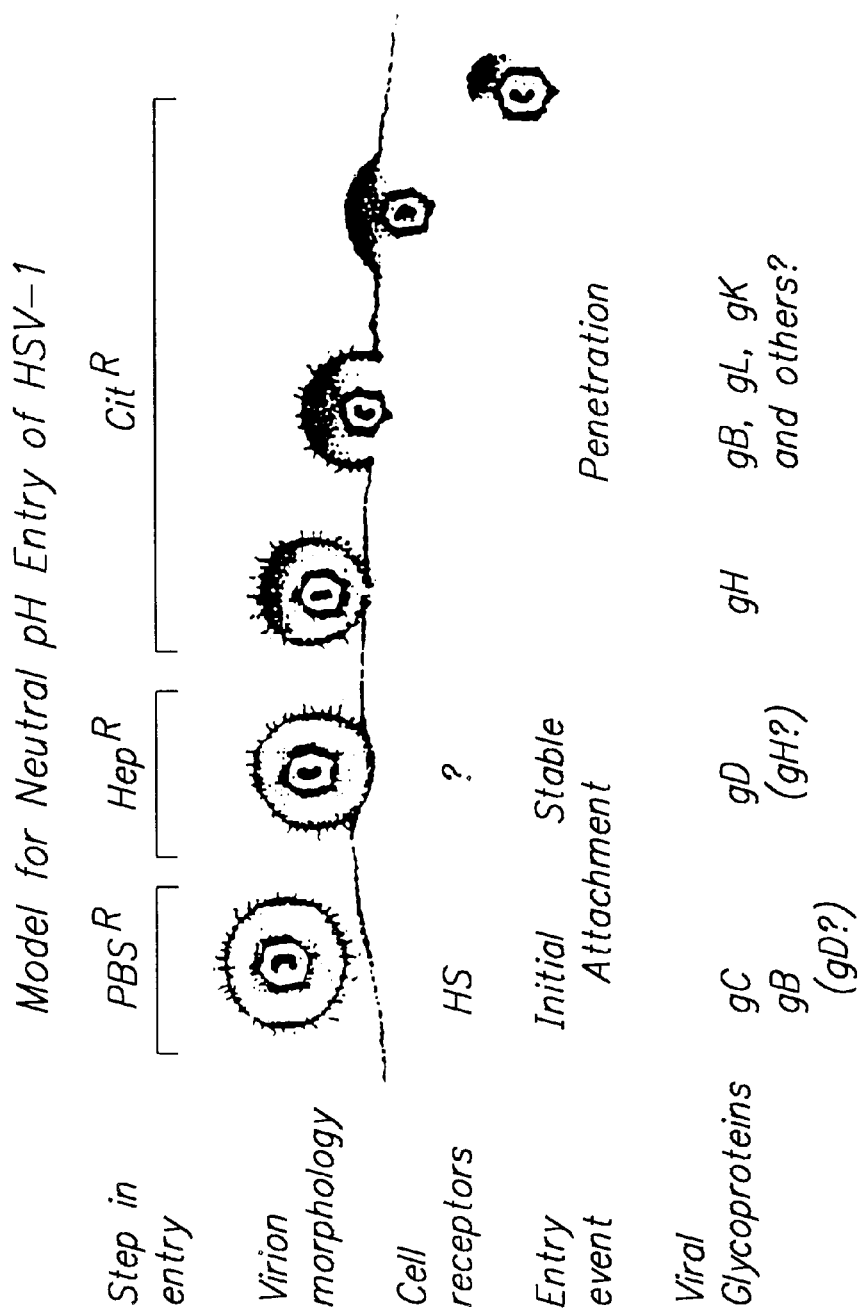
FIG. 1 is a schematic showing a model of pH independent entry of HSV. A working model of HSV entry shows the proposed multiple steps for entry, and receptors and viral proteins known to be involved in these events.

To facilitate understanding of the invention, a number of terms are defined below.

The term "HSV glycoprotein" refers to any of the glycoproteins found in the membrane region of HSV-1, HSV-2, and related herpes viruses. Presently preferred HSV glycoproteins are gB, gC, gD, gE/gI, and gH/gL. Included within this definition are glycoproteins extracted from natural viruses (e.g., from infected sera or cell culture), and glycoproteins produced by recombinant methods. Such glycoproteins may additionally be modified, either by chemical or enzymatic means (e.g., by proteolytic cleavage), or by recombinant DNA techniques (e.g., by fusing HSV glycoprotein genes with other genes to provide fusion proteins, or by deleting or replacing sections of the DNA sequence).

The term "HVEM" refers to the newly identified member of the tumor necrosis factor receptor (TNFR) family, called Herpes Virus Entry Mediator (HVEM)[See FIG. 4 for the nucleotide (SEQ ID NO:3) and amino acid (SEQ ID NO:4) sequence], recently reported to mediate HSV-1 entry into Chinese hamster ovary (CHO) cells.

The term "B5 or B5T74" refers to the newly identified gene encoding for an HSV polypeptide receptor of the present invention (See FIG. 5 and FIG. 6 for the nucleotide (SEQ ID NO:1) and amino acid (SEQ ID NO:2) sequence respectively). Transfection of eukaryotic cells (refractory to infection with HSV), with a vector containing the nucleic acids encoding for the HSV receptors of the present invention, renders the host cells permissive to HSV entry and replication.

The term "permissive" to HSV made in reference to a host cell indicates that the host cell allows human HSV strains to enter the host cell. Therefore, "non-permissive to HSV infection" means that the host cell does not allow the human virus to enter the host cell. Some non-permissive cells may nonetheless bind HSV (but not permit entry).

The term "endogenous" HSV receptors refers to a host cell expressing receptors which are naturally found in the cell. The term "heterologous" refers to HSV receptors which are not naturally expressed by the host cell. Heterologous receptors are not endogenous to the cell into which it is introduced, but have been obtained from another cell, such as, for e.g., the porcine cells are transfected with human cDNAs encoding for the HSV receptors in the present invention.

The term "gene" refers to a DNA sequence that comprises control and coding sequences necessary for the production of a polypeptide or its precursor. The polypeptide can be encoded by a full length coding sequence or by any portion of the coding sequence.

The term "nucleic acid sequence of interest" refers to any nucleic acid sequence, the manipulation of which may be deemed desirable for any reason by one of ordinary skill in the art (e.g., confer improved qualities).

The term "wild-type" when made in reference to a gene refers to a gene which has the characteristics of a gene isolated from a naturally occurring source. The term "wild-type" when made in reference to a gene product refers to a gene product which has the characteristics of a gene product isolated from a naturally occurring source. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and or functional properties (i.e., altered characteristics) when compared to the wild-type gene or gene product. It is noted that naturally-occuring mutants can be isolated; these are identified by the fact that they have altered characteristics when compared to the wild-type gene or gene product.

The term "recombinant" when made in reference to a DNA molecule refers to a DNA molecule which is comprised of segments of DNA joined together by means of molecular biological techniques. The term "recombinant" when made in reference to a protein or a polypeptide refers to a protein molecule which is expressed using a recombinant DNA molecule.

As used herein, the terms "vector" and "vehicle" are used interchangeably in reference to nucleic acid molecules that transfer DNA segment(s) from one cell to another.

The term "expression vector" or "expression cassette" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "targeting vector" or "targeting construct" refer to oligonucleotide sequences comprising a gene of interest flanked on either side by a recognition sequence which is capable of homologous recombination of the DNA sequence located between the flanking recognition sequences.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "means for transfecting eukaryotic cells" as used herein refers to rendering the cell transfected by the vectors containing the nucleic acids encoding for the HSV receptors in the present invention, by various means known to persons of skill. For instance, there are several well-known methods of introducing nucleic acids into animal cells. These include: calcium phosphate precipitation, fusion of the recipient cells with bacterial protoplasts containing the nucleic acid, treatment of the recipient cells with liposomes containing the nucleic acid, DEAE dextran, electroporation and micro-injection of the DNA directly into the cells.

The terms "infecting" and "infection" with a virus refer to co-incubation of a target biological sample, (e.g., cell, tissue, etc.) with the virus under conditions such that nucleic acid sequences contained within the virus are introduced into one or more cells of the target biological sample.

The term "transgenic" when used in reference to an animal refers to an animal which comprises a transgene, or whose genome has been altered by the introduction of a transgene. The term "transgenic" when used in reference to an animal which comprises one or more cells which contain a transgene, or whose genome has been altered by the introduction of a transgene. These transgenic cells and transgenic animals may be produced by several methods including the introduction of a "transgene" comprising nucleic acid (usually DNA) into a target cell or integration into a chromosome of a target cell by way of human intervention, such as by the methods described herein.

The term "transgene" as used herein refers to any nucleic acid sequence which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, etc.) relative to the naturally-occurring sequence. The term "heterologous DNA sequence" refers to a nucleotide sequence which is ligated to, or is manipulated to become ligated to, a nucleic acid sequence to which it is not ligated in nature, or to which it is ligated at a different location in nature.

Heterologous DNA is not endogenous to the cell into which it is introduced, but has been obtained from another cell. Heterologous DNA also includes an endogenous DNA sequence which contains some modification. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

As used herein, the term "probe" when made in reference to an oligonucleotide (i.e., a sequence of nucleotides) refers to an oligonucleotide, whether occurring naturally as in a purified restriction digest or produced synthetically, recombinantly or by PCR amplification, which is capable of hybridizing to another oligonucleotide of interest. A probe may be single-stranded or double-stranded; although when double-stranded, they are rendered single-stranded for hybridization. Probes are useful in the detection, identification and isolation of particular gene sequences. Oligonucleotide probes may be labelled with a "reporter molecule," so that the probe is detectable using a detection system. Detection systems include, but are not limited to, enzyme, fluorescent, radioactive, and luminescent systems.

The term "selectable marker" as used herein, refer to a gene which encodes an enzyme having an activity that confers resistance to an antibiotic or drug upon the cell in which the selectable marker is expressed. Selectable markers may be "positive" or "negative." Examples of positive selectable markers include the neomycin phosphotransferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The terms "promoter element," "promoter," or "promoter sequence" as used herein, refer to a DNA sequence that is located at the 5' end (i.e., precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The term "amplification" is defined as the production of additional copies of a nucleic acid sequence and is generally carried out using polymerase chain reaction technologies well known in the art. As used herein, the term "polymerase chain reaction" ("PCR") refers to the method of K. B. Mullis disclosed in U.S. Pat. Nos. 4,683,195, 4,683,202 and 4,965, 188, all of which are hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; and/or incorporation of $^{32}$P-labeled deoxyribonucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences may be used to obtain segments of DNA (e.g., genes) for the construction of targeting vectors, transgenes, etc.

As used herein, the terms "complementary" or "complementarity" when used in reference to polynucleotides refer to polynucleotides which are related by the base-pairing rules. For example, for the sequence 5'-AGT-3' is complementary to the sequence 5'-ACT-3'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective)

interaction. The absence of non-specific binding may be tested by the use of a second target which lacks even a partial degree of complementarity (e.g., less than about 30% identity); in the absence of non-specific binding the probe will not hybridize to the second non-complementary target.

When used in reference to nucleic acid hybridization, the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions.

"Stringency" when used in reference to nucleic acid hybridization typically occurs in a range from about $T_m$–5° C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" a nucleic acid sequence of interest will hybridize to its exact complement and closely related sequences.

Low stringency conditions when used in reference to nucleic acid hybridization comprise conditions equivalent to binding or hybridization at 42° C. in a solution consisting of 5× SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5× SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5× SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42° C. when a probe of about 500 nucleotides in length is employed.

As used herein, the term "purified" or "to purify" refers to the removal of contaminants from a sample. For example, recombinant HSV polypeptides, including HSV-GFP fusion proteins are purified by the removal of host cell components such as nucleic acids, lipopolysaccharide (e.g., endotoxin).

The term "oligonucleotide" as used herein is defined as a molecule comprised of two or more deoxyribonucleotides or ribonucleotides, usually more than three (3), and typically more than ten (10) and up to one hundred (100) or more (although preferably between twenty and thirty). The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The terms "nucleic acid substrate" and nucleic acid template" are used herein interchangeably and refer to a nucleic acid molecule which may comprise single- or double-stranded DNA or RNA.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

The term "sequence variation" as used herein refers to differences in nucleic acid sequence between two nucleic acid templates. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene. It should be noted that, while the invention does not require that a comparison be made between one or more forms of a gene to detect sequence variations, such comparisons are possible using particular hybridization conditions as described in U.S. Pat. No. 5,652,096, hereby incorporated by reference.

The term "$K_m$" as used herein refers to the Michaelis-Menton constant for an enzyme and is defined as the concentration of the specific substrate at which a given enzyme yields one-half its maximum velocity in an enzyme catalyzed reaction.

The term "nucleotide analog" as used herein refers to modified or non-naturally occurring nucleotides such as 7-deaza purines (i.e., 7-deaza-dATP and 7-deaza-dGTP). Nucleotide analogs include base analogs and comprise modified forms of deoxyribonucleotides as well as ribonucleotides. As used herein the term "nucleotide analog" when used in reference to substrates present in a PCR mixture refers to the use of nucleotides other than dATP, dGTP, dCTP and dTTP; thus, the use of dUTP (a naturally occurring dNTP) in a PCR would comprise the use of a nucleotide analog in the PCR. A PCR product generated using dUTP, 7-deaza-dATP, 7-deaza-dGTP or any other nucleotide analog in the reaction mixture is said to contain nucleotide analogs.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like.

A "consensus gene sequence" refers to a gene sequence which is derived by comparison of two or more gene sequences and which describes the nucleotides most often present in a given segment of the genes; the consensus sequence is the canonical sequence.

The term "polymorphic locus" is a locus present in a population which shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "bacteria" refers to any bacterial species including eubacterial and archaebacterial species.

The term "virus" refers to obligate, ultramicroscopic, intracellular parasites incapable of autonomous replication (i.e., replication requires the use of the host cell's machinery).

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is partially complementary to a reference sequence "GTATA".

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length B5 cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length B5 protein or enhancer cDNA sequences.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence (e.g., various fragments of the B5 protein). Fragments typically are at least 14 amino acids long, preferably at least 20 amino acids long, usually at least 50 amino acids long or longer, and span the portion of the polypeptide required for intermolecular binding of B5. The term "analog" as used herein refers to polypeptides which are comprised of a segment of at least 25 amino acids that has substantial identity to a portion of the deduced amino acid sequence of B5. The term "agent" is used herein to denote a chemical compound, a mixture of chemical compounds, a biological macromolecule, or an extract made from biological materials such as bacteria, plants, fungi, or animal (particularly mammalian) cells or tissues. Agents are evaluated for potential activity as antagonists of HSV receptors by inclusion in screening assays described herein below.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes (e.g., $^3$H), fluorescent labels (e.g., FITC, rhodamine, lanthanide phosphors), enzymatic labels (e.g., horseradish peroxidase, P-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. In others, the label is part of the fusion protein (e.g., GFP).

GENERAL DESCRIPTION OF INVENTION

The invention generally relates to compositions and methods of screening therapeutics against HSV infection, and in particular, compositions comprising receptors which enable cell specific entry of HSV.

The description of the invention involves A) HSV infection generally, B) the isolation of the HSV receptors, C) the construction of the expression vectors comprising nucleic acid encoding receptors, D) selection of the host cells, including but not limited to cells that are ordinarily refractory to HSV infection, E) introduction and detection of the expression construct into a particular cell, F) infection with HSV of the transfected, previously-refractory cells, G) drug screening.

A. HSV Infection

The primary steps of HSV infection allow viruses to attach and cross a biological membrane of host cells. This process is not well understood, but seems to occur in at least two ways. A pH-dependent route of entry requires attachment, engulfment into an endosomal vesicle and entry of the virus across the membrane of an intracellular vesicle. Binding of viral components to cellular receptors and pH change in an intracellular vesicle are key events to initiate membrane fusion for viral infection. However, the molecular mechanism(s) remain unclear. An alternative route, pH-independent entry, occurs at physiological pH and does not involve obvious pH change or require endocytosis (See FIG. 1). Transit of virus through the plasma membrane into the cell cytoplasm can occur without acidification to trigger conformational changes in viral or cellular proteins. The events that trigger changes in viral or cellular components to alter distribution of the lipid bilayer for virion penetration are not known. HSV, human immunodeficiency virus (HIV), measles virus, respiratory syncytia virus and many other pathogenic viruses can enter cells at neutral pH. Moreover, pH-independent membrane fusion seems to occur in cell division, fertilization, exocytosis and endocytosis.

HSV proteins: There are at least twelve viral glycoproteins encoded by HSV. They likely serve to bind the virus to cells, mediate events of entry and spread between cells and to modulate the host immune response. For HSV entry, a series of binding events between viral and cellular components appear to trigger changes in conformation of viral or cellular components. These changes result in lipid bilayer redistribution, membrane fusion and release of the nucleocapsid across a biological membrane. This process predicts several binding events and involvement of multiple viral or cellular components in fusion for entry or for viral-cell spread. Existence of many HSV envelope proteins, HSV glycoproteins gD, and possibly gH/gL are required for binding to non-HS receptors to mediate stable attachment and penetration. Other viral proteins including gB and gE/gI may be involved in cell spread or syncytia formation. Still others, gC, gK, may affect unknown events that influence entry or spread.

Eukaryotic cellular binding proteins

While precise mechanisms need not be known for the successful practice of the invention, it is believed that the B5 and HVEM proteins of the present invention, are involved in the attachment of HSV to cells or mediate cell surface events important for virion-cell fusion. There are at least two experimentally distinguishable types of attachment, initial and stable attachment. These attachments could require multiple viral components, or domains, and multiple cell surface components. The broad tissue and host range of HSV is consistent with requirements for variation in viral or cell proteins during lytic and latent phases of replication. The components and how they work together to result in membrane fusion for HSV entry is still unclear. Also, the mechanisms of HSV infection, whether common or different components on different cells are involved is poorly understood.

Heparan sulfate (HS) proteoglycans found on many tissues initially bind HSV to cells. Although HS enhances HSV binding, it is not required for entry or cell spread. Evidence indicates presence on susceptible cells of non-HS receptors that facilitate stable attachment. That HSV infects most cultured cells, has proven an obstacle in identifying and proving involvement of cellular proteins in HSV entry. Cell protein candidates that were thought to be "receptors" for HSV include basic fibroblast growth factor (bFGF) receptor and the mannose-6 phosphate receptor. A 62 kd band has been identified by anti-idiotype antibodies to gD. A clear role in HSV entry has not been established for any of these potential candidates.

Identification of receptor(s) that function in human cells and understanding how they mediate entry of HSV-1 and/or HSV-2 are critical to understanding of HSV tropism and immunopathogenesis. In the present invention, the herpes virus entry mediator protein (HVEM) and the B5 protein (isolated with porcine A7 cells) are described. In the porcine cell systems, human cDNA libraries were screened after transient transfection followed by infection with an indicator mutant HSV that expresses lacZ. HVEM is a novel member of the tumor necrosis factor alpha (TNFα) receptor family whose protein members contain characteristic structural features such as conserved position of cysteine residues. Although HVEM transcripts are found in most tissue, protein levels are low for most human cells with the exception of lymphocytes.

B. Isolation of HSV Receptors

A genetic approach was used to identify human genes that transfer HSV susceptibility to porcine cells by transfecting plasmids in a cDNA library, or total genomic DNA, into SK6-A7 cells. SK6-A7 cells are poorly susceptible clonal porcine cell lines (See Experimental Section for details). HSV-1 yields from SK6-A7 cells are six order of magnitude lower than those obtained from human cells. Like other porcine cells, A7 cells are defective in HSV entry, yet fully support HSV replication. To screen for porcine cells that become susceptible to HSV-1 infection several approaches were used. Infection by UV-inactivated virus was used to identify susceptible cells by Fluorescence Activated Cell Sorter (FACS). Mutant viruses that expresses the β-galactosidase gene were used to screen sequences in a cDNA library and detect porcine cells that become susceptible to HSV-1 infection. Cell sorting by FACS analysis yielded minimal results. However, screening of the cDNA library was more successful. After several rounds of screening, a pool containing plasmids from about 50 bacterial colonies consistently transferred HSV-1 susceptibility to swine cells. Southern blot analysis showed that HVEM is present in 11 out of 15 colonies screened. Several clones transfered susceptibility to A7 cells, but are negative for HVEM by Southern blot and PCR.

Cells and Viruses:

The clonal porcine SK6-A7 (A7) cell line was isolated and characterized as described in the Experimental Section. A7 cells were maintained in DMEM+5% FBS. HSV-1(F) [ATCC VR-733] was grown on HEp-2 cells and purified virus made with dextran gradients as previously described (Fuller, A. O., and P. G. Spear, 1987 Proc. Natl. Acad. Sci. USA. 84:5454–5458). An HSV-1(SC16) mutant that lacks gH and expresses β-galactosidase from the virus genome under the control of the CMV immediate early promoter and supporter cell line F6 were used. This mutant virus was propagated and titered on the supporter cell line F6. An HSV-1(KOS) mutant virus that lacks the ICP4 gene and expresses the β-galactosidase gene was grown on the supporter cell line E5 (DeLuca, N. A., A. M. McCarthy and P. A. Shaffer J. Virol. 56:558–570 1985). A mutant HSV-1 (KOS) that lacks the vhs sequences was grown on HEp-2 cells.

CDNA Library:

A cDNA library from human fetal lung cells was obtained from Invitrogen (San Diego, Calif.). The library contains DNA inserts that range from 0.95 kb to 2.3 kb with an average insert size of approximately 1.4 kb. The cDNAs are under the control of the IE CMV promoter in a pcDNA-1 vector. Bacteria colonies were grown on LB plates or broth with no more than 10 μg/ml of tetracycline and 40 μg/ml of ampicillin.

Transfections of SK6-A 7 Cells

For stable expression of human genomic DNA, cells were transfected by calcium phosphate. Fine precipitants were obtained by adding 31 μl of 2 M $CaCl_2$ to 250 μl of 2× N-2-hydroxyethylpiperazine-N-2-ethanesulfonic acid (HEPES)-buffered saline (pH 7.05) containing 10 μg of total human genomic DNA. A 500 μl volume of DNA precipitate was added to cells in a 60 mm dish and incubated at 37° C. for 30 min. Cells were overlaid with DMEM+5% FBS, incubated for 6 hr at 37° C. Media was removed and cells washed twice with warm PBS-A and overlaid with DMEM+ 5% FBS. At 48 hr post transfection cells were incubated in media containing 400 μg/ml of G418 (Geneticin, Sigma, St. Louis, Mo.) and selection continued for 10–14 days, after which cells were infected with HSV-1(F)[ ATCC 733].

For transient transfection, plasmids of a cDNA library were transfected into A7 by calcium phosphate as described above or by Lipofectin (Gibco-BRL, Life Technologies, Grand Island, N.Y.) following instructions of the manufacturer. At 48 hr post transfection cells were infected with mutant HSV-1 that encodes the β-galactosidase gene to test for cells that became susceptible to entry (Also, See Experimental Section).

Cell Sorting of Transfected A 7 Cells

Selected dishes of transfected cells were infected in suspension with UV-inactivated HSV-1(vhs-Δsma) at 37° C. for 1 hr. Cells were washed with heparin (100 μg) in PBS-A to remove virus that has not penetrated after the indicated time. Cells on ice were incubated with a mixture of monoclonal antibodies (500 μg each) against HSV-1 glycoproteins (I1-99-1 α-gD, II-512 α-gC, I-105 α-gB) for 30 min at 4° C. followed by an incubation with anti-mouse IgG FITC-conjugated (Sigma Co. St. Louis, Mo.). Samples were taken to the University of Michigan FACS facility for sterile sorting of HSV-1 infected cells. The top 1%–2% fluorescent cells were sorted and plated for growth. Sorted cells were maintained in DMEM media containing 20% FBS and 400 μg/ml of G418 (Gibco-BRL, Life Technologies, Grand Island, N.Y.).

Cell Sorting of HSV Susceptible Cells

As a different approach to identify human gene(s) that transfer HSV susceptibility, genetic transfer and cell sorting of HSV infected cells was used. HSV-1 infects cells by direct fusion of the virus envelope with the cellular membrane. During the process of virus entry, virion envelope proteins become an integral part of the cellular membrane. The amount of virus needed to detect signal from input virus on cell membrane was determined. HEp-2 cells were infected with UV-inactivated virus at different PFUs and presence of viral glycoproteins tested at 5 hr or 24 hr post infection by ELISA. Viral proteins were detected with as low as 10 PFU/cell at 5 hr post infection. No viral proteins were detected after 24 hr at any input. No cytopathic effect of infection was observed after 24 hours. Infection with 10 PFU-cell was used to detect viral envelope proteins deposited on the cell surface of cells competent for virus entry.

A7 cells were stably transfected with total genomic DNA or with a cDNA library and G418 resistant cells selected.

Transfected cells were split into sibling culture dishes. One culture dish was infected with HSV-1(SCgHZ) gH null virus that encodes the β-galactosidase gene. This identifies dishes that contained a high number of porcine cells which received receptor-encoding DNA and had become susceptible to HSV infection. Sibling dishes of those that were positive for HSV infection were used for cell sorting by FACS. Several sorting experiments were performed and HSV positive cells were grown and split into sibling dishes. Susceptible cells could be recovered and detected from sorted cells. However it was not possible to maintain the cells long term due to cell death in 5 days after sorting.

Screening of a cDNA Library for Genes That Transfer HSV Susceptibility

A cDNA library from human embryonic lung cells was used to screen for human genes that transfer HSV susceptibility to porcine cells. The cDNA library was initially expanded into 19 of 150 mm dishes and the expanded cDNA library was fractionated into several pools of samples. Pools of bacteria were grown in the appropriate media and plasmid DNA was isolated. A fraction of the bacteria broth was saved as a sample for further analysis of any positive transfer. SK6-A7 cells were transfected with 10 μg of plasmid DNA from different bacteria pools by lipofectin or calcium phosphate. At 30 or 48 hr post transfection, cells were infected with HSV-1(KOS) ICP4 or (SCgHZ) gH mutant virus that encodes for the β-galactosidase gene. These enter cells, express lacZ, but do not produce progeny virus to spread or infect other cells in the culture. At 30 or 48 hr post infection cells were strained for β-galactosidase expression. A cell that stained blue indicated that the cell had received a human gene that affected the ability of virus to infect A7 cells. Virus infections were initially at 10 PFU/cell, but were subsequently increased to 50 PFU/cell to obtain a stronger signal.

After several rounds of screening by transfection and expansion of positive pools, two groups that contained 25 bacterial colonies each were identified, that produced a significantly high number of blue A7 cells susceptible to HSV infection. Transfer of susceptibility with these pooled plasmids was consistent and reproducible. The two groups of 25 bacteria were separated into two groups of ten and one group of five. Each of these groups transferred susceptibility for HSV-1 infection to A7 cells. However, for two groups, A1 and B3, the number of blue foci were higher than for other groups.

During the screening process, a human gene, HVEM, from a HeLa cell cDNA library was identified that transferred HSV susceptibility to CHO cells. HVEM cDNA ws obtained and checked whether the plasmid encoding for HVEM was present in A1 and B3. A southern blot analysis of individual bacteria plasmid DNA from A1 and B3 were probed for HVEM and results indicated that 11 out of 15 colonies were positive for HVEM. Four of the plasmids were negative for HVEM, indicating the presence of genes that can transfer HSV susceptibility independent of HVEM.

Screening and expansion of one group of a human lung embryonic cDNA library produced two pools of 25 bacterial colonies that consistently transferred HSV susceptibility to A7 cells. Southern blot analysis showed that HVEM is present in those pools of bacteria. Therefore, genetic transfer using the porcine cells system yielded the isolation of at least HVEM. Plasmids that are positive for transfer of susceptibility, but negative for hybridization with HVEM, may encode human genes that are candidate HSV receptors.

Isolation and Sequencing of the HVEM cDNA

Another method employed for screening of HVEM is described below. A unidirectional HeLa cell cDNA expression library cloned into pcDNA1 in $E.coli$ (In Vitrogen, San Diego, Calif.) was plated onto 100 of 150 mm Luria-Bertani plates containing appropriate drugs ($1.5 \times 10^6$ bacteria/plate). Colonies were pooled by scraping and frozen as 100 glycerol stocks. Samples of each stock were combined into groups of 10 and grown to stationary phase in broth. Plasmids prepared from each culture were transfected into SK6-A7 (A7) cells using LipofectAMINE (Gibco BRL, Life Technologies, Grand Island, N.Y.); 1.5 ug of plasmid and 5 ul of LipofectAMINE/35 mm culture). For controls, cells were transfected with pMN84, a plasmid expressing β-galactosidase, or were incubated with LipofectAMINE alone. At 30 hr after transfection, the cells were washed, inoculated with KOS-gL86 (a β-galactosidase-expressing version of the HSV-1[KOS] gL86 strain, in which the $E. coli$ lacZ gene with the CMV promoter replaces part of the gL open reading frame) at about 100 pfu per cell, and then stained with X-gal as described (See Experimental Section; Infectivity Assays). Transfection efficiencies ranged from 30%–55% of cells based on expression of β-galactosidase from pMN84 in unifected cells. In the first round of screening the CDNA library, plasmids from one group of 10 bacterial stocks from the library converted about 20–30 cells in the monolayer to susceptibility to KOS-gL86 infection. The frequency of conversion to susceptibility was about 10 times higher for one of the 10 stocks in this group. This stock was divided again into 100 pools, and, by an iterative process, two bacterial clones were obtained that yielded plasmids (pBEC580 and pBEC748) with the desired phenotype. Both strands of the cDNA insert of pBEC580 were sequenced using Sequenase (Amersham) and T7 and Sp6 primers (obtained from the Northwestern University Biotechnology Center).

C. Construction of the Expression Vectors Comprising Nucleic Acid Encoding the HSV Receptors.

Plasmid Constructs of HVEM

Plasmid pBEC10, carrying the HVEM insert and a neomycin-resistance gene, was generated by cloning a Hindlll-Xhol fragment of pBEC580 into pcDNA3 (In Vitrogen, San Diego, Calif.). pBEC14 expressing HVEM-257Flu, was generated in several steps. The Hindlll-to-Sfil fragment of the HVEM insert from pBEC580 was modified by deletion between the BamH and BstYl sites, then inserted between Hindlll and EcoRl sites of pMN104 (blunt-end ligation between the Sfil and EcoRl sites after Klenow treatment).

pMN104 contains an oligonucleotide, inserted between the EcoRl and Xbal sites of pcDNA3, that encodes 11 amino acids (EFYPYDVPDYASL) plus a stop codon, including a 9 amino acid Flu epitope (underlined, Wilson et al.,Cell 37, 767–778, 1984) (SEQ ID NO:5). pMN a truncated Flu-tagged version of HSV-1 gL (M. J. Novotny and P.G.S., unpublished data). pBL58, expressing a hybrid form of HVEM (the ectodomain fused to the hinge, CH2 and CH3 domains of the rabbit 1gG heavy chain), was generated in several steps.

It consists of a cytomegalovirus promoter from pcDNA-neo (Spel to Hindlll); Hindlll to Xbal from pGEM3; the ectodomain of HVEM from pBEC580 (Nhel site to a Pvull site just downstream of the last Cys residue); a fragment of rabbit 1gG heavy chain cDNA from plasmid 3-4 (obtained from K. Knight at Loyola University Medical Center) including an EcoRl site added by polymerase chain reaction 5' to the rabbit sequence (SEQ ID NO:6) ACAAGAC-CGTGC and extending to a Pstl site downstream of the reading frame (after cleavage with EcoRl, the filled-in site was blunt end-ligated to the Hindlll site, and the Nhel site was ligated to the Spel site of the CMV promoter fragment). It is not intended that the present invention be limited by the nature of the expression vector. A variety of expression vectors comprising the nucleic acid encoding the receptor, are contemplated.

Plasmid Constructs of B5

The B5 cDNA of 1.2 kb was subcloned out of the original vector into pCDNA3.1,zeo/CAT (InVitrogen, San Diego, Calif.) that contains a zeocin resistant gene. It also was subcloned into pCDNA3/myc plasmid (to express a myc epitope tagged protein) (Also, See Experimental section).

D. Selection of Host Cells

The selection of host cells, includes but not limited to cells that are ordinarily refractory to HSV infection. A recent development for study of HSV entry and pathogenesis is the discovery that porcine cells are resistant to HSV infection due to a defect only at viral entry. This is true for cultured cell lines (ST, SK-6, others) and primary porcine cells. The defect in vitro to cultured cells is consistent with lack of susceptibility of infant pigs to infection by HSV-1 or HSV-2. Unlike other HSV entry-defective cell lines such as CHO cells, porcine cells are fully competent for HSV replication and other events in infection.

The present invention contemplates an entry defective clonal porcine cell system. This model system has facilitated cloning of human cDNAs of HSV receptor proteins, including B5T74, (B5) and herpes virus entry mediator (HVEM), that mediate entry and infection of HSV. The porcine system is useful to characterize structure and functions of human gene products in neutral pH HSV entry into porcine and other cells, and is likely to be identical to the process on native host human cells or other highly susceptible cells.

Development of Cell Model Systems for Studying Herpes Simplex Virus Types 1 and 2:

In the present invention, a cell culture system is developed in which cultured or primary cells can be made susceptible or poorly susceptible to infection with human pathogens HSV-1 and HSV-2 by transfection of specific human genes. The clonal cells include several clones of swine kidney cells, transformed swine cells from other tissues or primary porcine cells. The presence or absence of human herpes virus entry receptors (as well as other cloned human genes that can be specifically identified) is the only requirement to make the system support or not support HSV-1 and HSV-2 replication and infection. In this manner, the present invention provides a novel and powerful system for isolating and examining HSV interactions with cells during entry and penetration. This is the only cell system known to provide a single defect to HSV infection at a critical event of entry, that can be reversed by presence of a specific human gene product.

E. Introduction and Detection of the Expression Construct Into a Particular Cell Stable HVEM-expressing cell lines were produced by transfection of Clonal A7 porcine cells, CHO-K1 cells and Swine Testis (ST) cells with pBEC10 and selection in medium containing Geneticin (500ug/ml for CHO-K1 cells and 800 ug/ml for ST cells). Surviving cells were cloned by limiting dilution, and cell clones susceptible to KOS-gL86 infection were subcloned and expanded. Control cell lines were produced by transfecting porcine A7 cells, CHO-K1 and ST cells with pcDNA3 and isolating Geneticin-resistant clones.

Stable B5-expressing cell lines were produced by transient transfection of primary porcine cells, Clonal A7 porcine cells, CHO-K1 cells and ST cells with pCDNA3.1/ZEO/CAT (InVitrogen, San Diego, Calif.) and selection in medium containing zeomycin. (See Experimental section for details).

F. Infection with HSV of the Transfected, Previously-Refractory Cells.

Inrfectivity Assays:

Infectivity assays were based on quantitation of pgalactosidase expressed from the viral genome or by the β-galactosidase-expressing cell line CHO-IEB8. Adherent porcine or other cells were plated in 96 well tissue culture dishes ($2-4 \times 10^4$ cells/well) at least 16 hr prior to infection. Cells were washed and exposed to virus (in 50 ul of phosphate-buffered saline [PBS] containing glucose and 1% calf serum [PBS-G-CS] for 6 hr at 37° C. before solubilization in 100 ul of PBS containing 0.5% NP-40 and the β-galactosidase substrate, o-nitro-phenyl β-D-glucopyranoside (ONPG, 3 mg/ml). The reaction was monitored by spectrometry at several timepoints after the addition on ONPG to define the interval over which the generation of product was linear with time (Dynatech ALICE reader or a spectromax 250).

Aternatively, cells plated in 6 well tissue-culture dishes were exposed to virus and infected cells visualized using the β-galactosidase substrate X-gal (GIBCO Laboratories), which yields an insoluble blue reaction product. After infection, washed cells were fixed (PBS containing 2% formaldehyde and 0.2% glutaraldehyde), permeabilized (2 mM MgCl2 containing 0.01% deoxycholate and 0.02% NP-40), and incubated with buffered X-gal (0.5 mg/ml).

G. Drug Screening

The present invention identifies suitable porcine cell systems as models, and screening assays employing HSV specific receptors for the design of vaccines and therapeutics against HSV infection. Screening assays are described further in the Detailed Description.

DETAILED DESCRIPTION AND USES OF THE INVENTION

The present invention contemplates testing compounds using herpes simplex virus and cells containing and lacking receptors for such viruses. It is not intended that the present invention be limited to particular receptors. However, the isolation of illustrative receptors (and corresponding nucleic acid encoding such receptors) useful in the methods of the present invention are described below.

A. Purified Herpes Simplex Virus Receptors

The present invention provides a purified herpes simplex virus receptor B5 polypeptide having the amino acid sequence set forth in the Sequence Listing as SEQ ID NO: 2, as well as fragments and variants thereof. By "purified" is meant more pure than the compound exists in nature and pure enough for use in an assay, e.g., more pure than a cellular extract containing the receptor. This definition contemplates a polypeptide that is essentially free of normally present cellular components such as nucleic acids not part of the gene for the polypeptide, and cellular structures. An example of a purified polypeptide of the invention is a HSV receptor in a protein extract from a cell that does not normally express the receptor, but has been transfected or transformed to express the receptor as described below.

Another example of a purified polypeptide is an in vitro synthesized polypeptide, obtained using a cell-free translation system or a linked transcription-translation system. Direct synthesis is also a method of obtaining a purified receptor or fragment of the invention. Purification of the receptor or fragment produced by any method can be accomplished by a number of routine methods and combinations of methods such as electrophoresis, blotting, precipitation, immunoprecipitation, dialysis, chromatography or combinations of these and other methods.

The present invention also provides for purified homologs of the herpes simplex virus receptor. Such homologs may be obtained from a human or other primate species whose genome encodes a homolog of the present herpes simplex virus receptor. Methods used to isolate a nucleic acid encoding a homolog to the purified herpes virus receptor of SEQ ID NO: 2 include, but are not limited to, screening the genome of a species believed to encode a herpes simplex virus homolog by nucleic acid hybridization methods or through polymerase chain reaction (PCR) techniques (e.g., using portions of the nucleic acid sequences set forth in SEQ ID NOS: 1 and 3 as primers and probes). Materials suitable for screening include, but are not limited to, cDNA or genomic libraries of the appropriate animal cloned into lambda, cosmid, yeast, mammalian, or plasmid cloning vectors, DNA isolated and subjected to Southern blot analysis, RNA isolated and subjected to Northern blot analysis, and isolated DNA or RNA used as a template for PCR.

The invention provides purified polypeptide fragments of the HSV receptor that have virus binding activity. Fragments including those encoded by the nucleic acids of the present invention are also contemplated. The polypeptide fragments of the present invention can be recombinant proteins obtained by cloning nucleic acids encoding the polypeptide in an expression system capable of producing the polypeptide or fragments thereof. The purified HSV binding domain can be used in drug screening, purification of HSV from a sample, detection of HSV in a sample, and other assays as described below.

The invention also provides purified polypeptide fragments of HSV receptors that regulate virus binding activity at a virus binding domain of the HSV receptor. Fragments including those encoded by the nucleic acids of the present invention are also contemplated. The polypeptide fragments of the present invention can also be recombinant proteins obtained by cloning nucleic acids encoding the polypeptide in an expression system capable of producing the polypeptide or fragments thereof. The purified HSV receptor regulatory domain can be utilized in a system to regulate the binding activity of endogenous HSV receptors, in a research setting to investigate the method of regulation of HSV binding proteins, or as a model to investigate the regulation of ligand binding proteins.

The purified polypeptides can be tested to determine their activity and specificity by the methods taught herein. Active fragments of the polypeptide can also be synthesized directly, expressed as recombinant peptides (including fusion peptides) or obtained by chemical or mechanical disruption of larger polypeptides. An active fragment is defined as an amino acid sequence of at least about 5 consecutive amino acids derived from the naturally occurring amino acid sequence, which has the relevant activity, e.g., binding or regulatory activity. Once the amino acid sequence of the polypeptide is provided, it is also possible to synthesize, using standard peptide synthesis techniques, peptide fragments chosen to be homologous to active regions of the receptor. Fragments of the HSV receptor possessing an activity of the receptor can be obtained by mechanical or chemical disruption of the receptor protein, followed by fractionation. Thus, synthesis or purification of an extremely large number of fragments derived from the polypeptide is possible.

The entire polypeptide or fragments can be attached to sequences designed to provide for some additional property, such as solubility. The fragments, whether attached to other sequences or not, can also include insertions, deletions, substitutions, or other selected modifications of particular regions or specific amino acids residues, provided the activity of the peptide is not significantly altered or impaired compared to the native polypeptide or fragment thereof. These modifications to a fragment of the HSV receptor can provide for some additional property, such as to remove/add amino acids capable of disulfide bonding, to increase its bio-longevity, etc. In any case, the peptide must possess a bioactive property, such as binding activity, regulation of binding at the binding domain, etc. Functional or active regions of the HSV virus receptor may be identified by mutagenesis of a specific region of the receptor, followed by expression and testing of the expressed polypeptide (or expression in a cell and testing the cell for susceptibility to HSV infection). Such methods are readily apparent to a skilled practitioner in the art and can include site-specific mutagenesis of the nucleic acid encoding the receptor. (Zoller, M. J. and Smith, M. Oligonucleotide-directed mutagenesis using M13-derived vectors: an efficient and general procedure for production of point mutations in any fragment of DNA. *Nuc. Acids Res.* 10: 6487–6500 (1982)).

The invention also provides the purified HSV receptor or fragment (e.g., binding domain or regulatory domain) bound to a solid support. Examples of suitable substrates include, but are not limited to, polymers, beads (e.g., agarose, polystyrene, sepharose, etc.), latex plates, glass or plastic petri or culture dishes, albumin, and the like. Other suitable substrates can be selected by referring to standard references, e.g., Harlow and Lane, Antibodies: A Laboratory Manual, Cold Spring Harbor Laboratory, Cold Spring Harbor, N.Y., (1988).

Uses contemplated for this immobilized HSV receptor include, but are not limited to, affinity chromatography techniques such as those used to concentrate specific molecules which bind to the receptor, in this example, such as HSV proteins and viral proteins. The immobilized receptor can be used to identify other natural or artificial ligands. Techniques used to determine the concentration of HSV in a sample, such as enzyme linked immunosorbent assay and techniques used to purify HSV from contaminants in a sample comprising contacting the sample with immobilized HSV receptor followed by removing the immobilized HSV receptor and the HSV bound to the receptor from the sample, thereby purifying the HSV from the impurities in the sample are provided. Assays used to determine the effect specific compounds have on the ability of HSV to bind to a HSV receptor are also provided as described below.

B. Nucleic Acids

The present invention provides an isolated nucleic acid comprising the nucleic acid encoding a purified HSV receptor polypeptide, said polypeptide having the sequence set forth in the Sequence Listing as SEQ ID NO: 2. This nucleic acid can be the nucleic acid having the sequence set forth in the Sequence Listing as SEQ ID NO: 1. The DNA sequence shown in SEQ ID NO: 1 is a 1287bp nucleic acid encoding the polypeptide set forth in the Sequence Listing as SEQ ID NO: 2. The nucleic acid can be any other sequence of nucleotides that encodes the polypeptide set forth in the Sequence Listing as SEQ ID NO: 2. The nucleic acids of the invention can be double-stranded or can be in denatured (single-stranded) form. The invention includes DNA having the recited sequences and its complement, and RNAs which correspond to the DNA.

Also provided is a nucleic acid that encodes a polypeptide comprising the HSV receptor binding domain or fragment of the receptor having binding activity. Also provided is a nucleic acid that encodes a polypeptide comprising HSV receptor regulatory domains or fragment of the receptor having regulatory activity. Such regulatory domains can be manipulated through recombinant techniques well known in the art to alter their activity and or effect on other regions of a herpes simplex virus receptor. Similarly, such regulatory regions may also be manipulated through recombinant techniques well known in the art to alter their activity and/or effect on other regions of a herpes simplex virus receptor or a herpes simplex virus binding domain.

By "isolated nucleic acid" is meant essentially separated from other genes and cellular material found in the organism. The nucleic acids of the present invention can include positive and negative strand RNA as well as DNA and includes genomic and subgenomic nucleic acids present in an organism. The nucleic acids contemplated by the present invention include a cDNA encoding the HSV receptor, the genomic DNA fragment containing the relevant introns and exons, as well as any upstream or downstream regulatory regions, the mRNA encoded by either the cDNA or the genomic DNA, and any nucleic acid which can hybridize to or encode the HSV receptor.

As used herein to describe nucleic acids, the term "selectively hybridizes" excludes the occasional randomly hybridizing nucleic acids. The selectively hybridizing nucleic acids can be used, for example, as probes or primers for detecting the presence of the nucleic acid encoding herpes simplex virus receptor (e.g., all or a portion of the nucleic acid provided in SEQ ID NO: 1), or a homolog thereof, that has the nucleic acid to which the primer or probe hybridizes.

The selectively hybridizing nucleic acids of the invention can have at least 60%, more preferably, 80%, still more preferably 90% or greater complementarity with the segment of the sequence to which it hybridizes. The nucleic acids can be at least 12 to 4000 nucleotides in length. Thus, the nucleic acid can be a coding sequence for the herpes simplex virus receptor of SEQ ID NO:2 or a homolog thereof or a fragment, or it can be used as a probe or primer for detecting the presence of the receptor. If used as primers, the invention provides compositions including at least two nucleic acids which selectively hybridize with different regions of the target nucleic acid so as to amplify a desired region. Depending on the length of the probe or primer, the target region can range between 70% complementary bases and complete complementarity and still hybridize under the stringency conditions described herein.

For example, for the purpose of detecting the presence of the herpes simplex virus receptor, the degree of complementarity between the hybridizing nucleic acid (probe or primer) and the sequence to which it hybridizes (DNA or RNA from a sample) is at least enough to exclude significant hybridization with a nucleic acid from unrelated (nonhomologous) receptors or unrelated HSV binding proteins. By "significant hybridization" is meant that a hybridization assay can distinguish between the herpes simplex virus receptor of the present invention or a homolog to the herpes simplex virus receptor and a nucleic acid from a nonhomologous gene or polynucleotide. Thus, a nucleic acid that selectively hybridizes with the nucleic acid encoding a herpes simplex virus receptor sequence (such as the nucleic acid set forth in SEQ ID NO: 1) will not selectively hybridize, under the stringency conditions described herein, with a nucleic acid of a segment of another, nonhomologous receptor, and vice versa.

Modifications to the nucleic acids of the invention are also contemplated as long as the essential structure and function of the polypeptide encoded by the nucleic acids is maintained. Likewise, fragments used as primers or probes can have substitutions so long as enough complementary bases exist for selective hybridization [Kunkel et al., *Methods Enzymol.* 154: 367 (1987)].

The nucleic acids described herein can be used to detect the nucleic acid of the present invention in samples by methods such as the polymerase chain reaction, ligase chain reaction, hybridization, and the like. Alternatively, these sequences can be utilized to produce an antigenic protein or protein fragment, or an active protein or protein fragment.

In addition, fragments of the nucleic acids described herein can be selected to selectively or specifically hybridize with homologous nucleic acids present in other animals or humans. Such a nucleotide sequence shared with other organisms can be used, for example, to simultaneously detect related sequences for cloning of homologs of the nucleic acid of the present invention encoding a herpes simplex virus receptor polypeptide.

An isolated nucleic acid capable of selectively amplifying any region of the HSV receptor gene of the present invention is contemplated. Available computer programs can be used to compare the sequence to select the most appropriate sequences for amplification primers and hybridization probes.

C. Virus Detection (Diagnosis) Methods

The invention provides a method of detecting the presence of herpes simplex virus in a sample, comprising contacting the purified herpes simplex virus receptor with a sample and detecting the presence of binding of herpes simplex virus to the purified receptor, the presence of binding indicating the presence of herpes simplex virus in the sample. For example, the purified herpes simplex virus receptor comprising the polypeptide sequence set forth in the Sequence Listing as SEQ ID NO:2 can be utilized in a method to determine the presence of herpes simplex virus in a sample. A fragment of the receptor that has HSV binding activity, for example a binding domain, can also be used to bind, and thus, detect HSV in a sample. As contemplated herein, purified receptor fragments include any portion of the receptor which binds herpes simplex virus.

One example of a method of detecting herpes simplex virus in a sample is performed by contacting a fluid or tissue sample from a subject with an amount of purified herpes simplex virus receptor or a binding domain of a herpes simplex virus receptor and detecting the binding of the receptor with the virus or an empty capsid of the virus. The fluid sample of this method can comprise any body fluid which would contain the virus or a cell containing the virus, such as, but not limited to, blood, plasma, serum, saliva, semen, feces, or urine. Other possible examples of body fluids include sputum, mucus, gastric juice, and the like. The tissue sample of this method can comprise any tissue obtained from a subject or patient, such as, but not limited to, brain tissue, liver tissue, kidney tissue, heart tissue, lung tissue, placenta tissue, skin tissue, muscle tissue, pancreatic tissue, and so forth. Such tissue samples can be prepared for analysis by disruption and separation into fractions based on size or density, or lysed for analysis of the cellular extracts. Other methods for tissue preparation are common and obvious to a skilled practitioner in the relevant art.

In one embodiment of the present HSV detection method, the presence of binding is determined by an immunoassay. Immunoassays such as immunofluorescence assays (IFA), enzyme linked immunosorbent assays (ELISA), and immunoblotting assays can be readily adapted to accomplish the detection of the HSV bound to the receptor. An ELISA method effective for the detection of the virus can, for example, be as follows: (1) bind the receptor to a substrate; (2) contact the bound receptor with a fluid or tissue sample containing the virus; (3) contact the above with a specific antibody bound to a detectable moiety (e.g., horseradish peroxidase enzyme or alkaline phosphatase enzyme); (4) contact the above with the substrate for the enzyme; (5) contact the above with a color reagent; and (6) observe color change. The above method can be readily modified to detect presence of the receptor as well as the virus.

Another immunologic technique that can be useful in the detection of HSV is a competitive inhibition assay wherein herpes simplex virus can be detected by competitive inhibition of receptor utilizing monoclonal antibodies (MABs) specifically reactive with the receptor. Briefly, sera or other body fluids from the subject is reacted with the receptor bound to a substrate (e.g., an ELISA 96-well plate). Excess sera is thoroughly washed away. A labeled (enzyme-linked, fluorescent, radioactive, etc.) monoclonal antibody is then reacted with the previously reacted herpes simplex virus-receptor complex. The amount of inhibition of monoclonal antibody binding is measured relative to a control. MABs can also be used for detection directly in samples by IFA for MABs specifically reactive for the receptor-virus complex.

Alternatively, a herpes simplex virus and/or a patient's antibodies to the virus can be detected utilizing a capture assay. Briefly, to detect antibodies to herpes simplex virus in a patient sample, antibodies to the patient's immunoglobulin, e.g., anti-IgG (or IgM) are bound to a solid phase substrate and used to capture the patient's immunoglobulin from serum. A herpes simplex virus, or reactive fragments of a herpes simplex virus, are then contacted with the solid phase followed by addition of a labeled receptor. The amount of patient herpes simplex virus specific antibody can then be quantitated by the amount of labeled receptor binding.

Additionally, a micro-agglutination test can also be used to detect the presence of herpes simplex virus in test samples. Briefly, latex beads are coated with the receptor and mixed with a test sample, such that herpes simplex virus in the tissue or body fluids that are specifically reactive with the receptor crosslink with the receptor, causing agglutination. The agglutinated receptor-virus complexes form a precipitate, visible with the naked eye or detectable by a spectrophotometer.

In the diagnostic methods described above, the sample can be taken directly from the patient or in a partially purified form. The receptor specific for herpes simplex virus reacts by binding the virus (the primary reaction). Thereafter, a secondary reaction with an anti-HSV antibody bound to, or labeled with, a detectable moiety can be added to enhance the detection of the primary reaction. Generally, in the secondary reaction, an antibody or other ligand which is reactive, either specifically or nonspecifically with a different binding site (epitope) of the receptor or the virus will be selected for its ability to react with multiple sites on the complex of receptor and virus. Thus, for example, several molecules of the antibody in the secondary reaction can react with each complex formed by the primary reaction, making the primary reaction more detectable.

The detectable moiety can allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy) and alkaline phosphatase (for biochemical detection by color change). The detection methods and moieties used can be selected, for example, from the list above or other suitable examples by the standard criteria applied to such selections (Harlow and Lane, Antibodies: A Laboratory Manual, Cold Spring Harbor Laboratory, Cold Spring Harbor, N.Y., (1988)).

The bound herpes simplex virus receptor or binding domain of the herpes simplex virus receptor of the present invention can be used to detect the presence of a herpes simplex virus specifically reactive with the herpes simplex virus receptor or a reactive fragment thereof. One skilled in the art can also appreciate that the herpes simplex virus bound to a solid support of the present invention can also be designed for virus neutralization testing and/or capture immunoassays in the methods described herein for removal/purification of herpes simplex virus.

D. Prevention and Treatment Methods

One embodiment of the present invention is a method of treating a subject infected with herpes simplex virus, comprising administering to the subject a therapeutically effective amount of a purified herpes simplex virus receptor and a pharmaceutically acceptable carrier. In this method, the herpes simplex virus receptor can be the receptor comprising the polypeptide set forth in the Sequence Listing as SEQ ID NO: 2.

Another embodiment provided for by the present invention is a method of preventing in a subject herpes simplex virus infection, comprising administering to the subject a prophylactically effective amount of a purified herpes simplex virus receptor and a pharmaceutically acceptable carrier. The herpes simplex virus receptor can be the receptor comprising the polypeptide set forth in the Sequence Listing as SEQ ID NO: 2.

In a specific embodiment, the present invention provides a herpes simplex virus receptor or a binding domain of a herpes simplex virus receptor, in a pharmaceutically acceptable carrier in an amount sufficient to administer to a human to prevent or treat an infection by herpes simplex virus.

Treatment or prevention of herpes simplex virus infection can be facilitated by competitive inhibition of herpes simplex virus binding to a cell by administration of exogenous herpes simplex virus receptor or a binding domain of a herpes simplex virus receptor in a pharmaceutically acceptable carrier.

The amount of herpes simplex virus receptor or a binding domain of a herpes simplex virus receptor that would be sufficient to treat a herpes simplex virus infection in a human depends on the amount of herpes simplex virus receptor or a binding domain of a herpes simplex virus receptor on the cells of the human subject. The dose can be determined by optimization procedures. The amount of herpes simplex virus receptor or a binding domain of a herpes simplex virus receptor will also vary depending upon the weight, size, and health of the human subject, and with the severity of herpes simplex virus infection.

In addition, given the discovery of the nucleic acid encoding a herpes simplex virus receptor as a cellular receptor for herpes simplex virus, antagonists which specifically bind to a herpes simplex virus receptor or a binding domain of a herpes simplex virus receptor and antagonize the binding of herpes simplex virus are also provided. The antagonist can be an antibody or a chemical which binds the receptor or otherwise alters the receptor or interferes with the interaction of virus and receptor. For example, utilizing methods taught in the Examples and other methods known in the art, one can select a chemical which reacts with the binding site of the herpes simplex virus receptor or a binding domain of a herpes simplex virus receptor to antagonize binding of herpes simplex virus. Empty herpes simplex virus capsids can be utilized as the antagonist. Alternatively, anti-idiotype and anti-anti-idiotype antibodies to both a herpes simplex virus receptor or a binding domain of a herpes simplex virus receptor and the herpes simplex virus can be utilized for prophylaxis or therapy. Naturally, the treatment modality can be selected to minimize any adverse side effects such as immune system recognition and deletion of the desirable herpes simplex virus receptor expressing cells. Thus, the invention also provides methods of screening for compounds which antagonize the binding of herpes simplex virus.

An embodiment of the present invention is a method of determining the anti-herpes simplex virus binding activity of a compound, comprising contacting the purified herpes simplex virus receptor with the compound and with herpes simplex virus and determining the relative amount of herpes simplex virus bound to the receptor, the relative amount of virus bound to the receptor being an indication of the anti-herpes simplex virus binding activity of the compound. The herpes simplex virus receptor can be on a cell which expresses the receptor. The herpes simplex virus receptor can be the receptor comprising the polypeptide set forth in the Sequence Listing as SEQ ID NO: 2.

Depending on whether the compound selected by the screening method is administered orally, parenterally, or otherwise, the compounds of the present invention can be in pharmaceutical compositions in the form of solid, semi-solid, or liquid dosage forms, such as, for example, tablets, pills, capsules, powders, liquids, and suspensions, or the like, preferably in unit dosage form suitable for delivery of a precise dosage. The compositions will include, as noted above, an effective amount of the selected compound in combination with a pharmaceutically acceptable carrier and, in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the selected compound without causing any undesirable biological effects or interacting in a deleterious manner with any of the other components of the pharmaceutical composition in which it is contained. Actual methods of preparing such dosage forms are known, or will be apparent, to those skilled in this art; for example, see Remington's Pharmaceutical Sciences, latest edition (Mack Publishing Co., Easton, Pa.).

Patients can also be treated orally with compositions of a herpes simplex virus receptor or a binding domain of a herpes simplex virus receptor to block infection from herpes simplex virus or to block transmission of herpes simplex virus. For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Also provided by the present invention is a method of preventing or treating herpes simplex virus infection in a human subject comprising preventing the binding of herpes simplex virus to a herpes simplex virus receptor or a binding domain of a herpes simplex virus receptor or other ligand by administering to the subject a composition comprising a herpes simplex virus receptor or a binding domain of a herpes simplex virus receptor which blocks the binding of herpes simplex virus to a herpes simplex virus receptor, binding domain, or natural ligand, thereby preventing or treating injection by the herpes simplex virus in the subject. As previously stated, the amount of the herpes simplex virus receptor or herpes simplex virus binding domain used in the method will depend upon many factors including the route of administration, relative potency of the composition and size and health of the patient. It is contemplated herein that a herpes simplex virus receptor or a binding domain of a herpes simplex virus receptor, or any portion of a herpes simplex virus receptor or binding domain of a herpes simplex virus receptor molecule reactive with herpes simplex virus can be utilized in the method to treat or prevent infection by herpes simplex virus.

Herpes simplex virus infection can also be prevented or treated by administering to the subject an antibody or other ligand reactive with a herpes simplex virus receptor or binding domain of other purified receptors which blocks the herpes simplex virus binding domain. The amount of antibody administered will also be dependent upon the mount of herpes simplex virus receptor on the cells of the subject and can be determined by optimization procedures as discussed herein.

By utilizing methods of identification and purification of the receptor taught herein, one skilled in the art can identify other herpes simplex virus receptors which can be utilized to prevent or treat herpes simplex virus infections in other species. For example, the purified receptor for monkey herpes simplex virus can be utilized in a composition to prevent or treat infection or to block transmission of the virus in a monkey utilizing methods for preparing the composition and optimization procedures for therapy described herein.

The present invention also provides a herpes simplex virus capable of infecting cells which express a herpes simplex virus receptor or binding domain of a herpes simplex virus receptor, wherein the herpes simplex virus has a human derived gene inserted into the herpes simplex virus genome. As a result of the discovery of the herpes simplex virus receptor, one skilled in the art can readily appreciate that herpes simplex virus or an attenuated strain can be utilized as a vector system to deliver herpes simplex virus to herpes simplex virus receptor expressing cells. Such methods are well known in the art and can be utilized by established procedures. (Sambrook et al., Molecular Cloning: A Laboratory Manual, 2nd Ed., Cold Spring Harbor Laboratory, Cold Spring Harbor, N.Y., (1989)).

Also provided is a method of introducing a therapeutant into a cell, comprising a therapeutant linked to or packaged within a herpes simplex virus capable of binding to the herpes simplex virus receptor or binding domain of a herpes simplex virus receptor of the present invention. A therapeutically effective amount of the therapeutant described above comprising the therapeutant and a pharmaceutically acceptable carrier discussed herein is contemplated. Such therapeutants comprise antibodies directed toward herpes simplex virus or a herpes simplex virus receptor or a binding domain of a herpes simplex virus receptor, drugs, compounds, or substances which may alter the binding of herpes simplex virus to a herpes simplex virus receptor or a binding domain of the herpes simplex virus receptor, fragments of a herpes simplex virus which bind to a herpes simplex virus receptor or a binding domain of a herpes simplex virus receptor, other natural or synthetic ligands which bind to a herpes simplex virus receptor or a binding domain of a herpes simplex virus receptor linked to a drug, compound, or other substance, or antibodies to a herpes simplex virus receptor or binding domain of a herpes simplex virus receptor linked to a drug, compound, or other substance.

E. Method of Producing HSV

The present invention also provides cells manipulated to have levels of herpes simplex virus receptor expressed on the cell surface which are increased over non-manipulated cells. The cells contemplated herein can be manipulated to contain increased levels of herpes simplex virus receptor or binding domain of herpes simplex virus or fragments thereof which act as a receptor for herpes simplex virus. One skilled in the art can appreciate that these cells can be manipulated in many ways including direct addition of herpes simplex virus receptor or binding domain of herpes simplex virus to cells with subsequent incorporation by mass action into the lipid bilayer of the cell. The manipulated cells of the present invention can include cells originally non-permissive for herpes simplex virus infection as well as permissive cells made more permissive. Examples of such cells include, but are not limited to, the porcine cell system of the present invention, neural ganglia, lymphocytes, hematopoietic stem cells or tumor cells.

Also provided by the present invention are cells expressing a foreign gene encoding a herpes simplex virus receptor or a binding domain of a herpes simplex virus receptor. Such cells include prokaryotic cells such as *E. coli*, or eukaryotic cells, such as COS-1 cells. Foreign genes can be introduced into these cells in a number of techniques, including, but not limited to, transfection, transformation, electroporation, injection, microinjection, and the like. Specifically, transfection includes techniques such as calcium phosphate coprecipitation, DEAE-Dextran mediated transfection, and lipofection. Viral vectors may also be utilized to introduce foreign genes into host cells. Cells expressing the foreign gene may therefore express the polypeptide encoded by the foreign gene on the cell surface. Such cells may therefore be infectable by herpes simplex virus and utilized either as models for studying infection of cells by herpes simplex virus, or as cells producing herpes simplex virus post-infection. A preferred embodiment of the present invention is a cell containing the nucleic acid encoded by the sequence set forth in the Sequence Listing as SEQ ID NO: 1.

F. Augmentation of Virus Vector Efficiency

The invention provides a method of delivering a desired gene into a cell expressing the herpes simplex virus receptor or binding domain of herpes simplex virus comprising infecting the cell with a non-virulent (modified) herpes simplex virus having the desired gene inserted into the herpes simplex virus genome. The present invention also provides a method of augmenting the above method, comprising increasing the amount of herpes simplex virus receptor or binding domain of herpes simplex virus expressed on the cell surface and infecting the cell with a herpes simplex virus having the desired gene inserted into the herpes simplex virus genome. One skilled in the art will readily appreciate that the identification of herpes simplex virus receptor, as taught by the present invention, enables methods of gene therapy with herpes simplex virus as the vector system. The desired human DNA fragment can be easily inserted into a host cell, e.g., one with sufficient levels of herpes simplex virus receptor or binding domain of herpes simplex virus on the cell surface as discussed herein utilizing methods known in the art, for example, See, Nienhuis, A. W., et al., Marcel Dekker, New York (1993).

G. Purification of HSV From a Sample

Another embodiment of the present invention provides a method of separating a herpes simplex virus from impurities in a sample, comprising binding herpes simplex virus with a purified herpes simplex virus receptor or binding domain of herpes simplex virus and separating the bound herpes simplex virus from the unbound impurities in the sample, thereby separating the herpes simplex virus from impurities in the sample. A preferred embodiment of the present invention is where the herpes simplex virus receptor is the receptor comprising the polypeptide set forth in the Sequence Listing as SEQ ID NO: 2. One skilled in the art will appreciate, based on the teaching herein, that purification of herpes simplex virus can be accomplished by the use of immobilized receptor, or receptor fragments that specifically bind the target herpes simplex virus. Once a complex of receptor and virus is formed, the impurities in a sample can be separated using techniques well known in the art and set forth herein, such as column purification and centrifugation.

H. Removal of HSV From Lesions and Secretions

The present invention provides a method for removing HSV from a sample comprising binding the HSV in the sample with a purified receptor for the virus or an active HSV binding fragment thereof and separating the bound virus from the infected cells, thereby removing the HSV from the tissue sample. The method of the present invention utilizes the receptor for HSV, e.g., the receptor of SEQ ID NO: 2 or homologs thereof, to bind to the virus. The bound complex can be removed from the infected sample by preparing a column with the immobilized receptor. The sample is then passed through the column, thereby removing HSV from the sample utilizing the binding affinity of HSV for the receptor. Alternatively, the immobilized receptor can be mixed with the sample and the bound virus-receptor complex removed by centrifugation.

I. Transgenic Animals

Transgenic animals expressing the HSV receptor of the present invention are also contemplated. Specifically, a non-human transgenic animal expressing a nucleic acid encoding a HSV receptor having the polypeptide sequence set forth as SEQ ID NO: 2, but not expressing an endogenous active herpes simplex virus receptor is contemplated. In this embodiment, the foreign nucleic acid expressed in the animal is a sequence comprising the sequence set forth in the Sequence Listing as SEQ ID NO: 1. Another embodiment of the present invention is a transgenic animal expressing the sequence encoding the herpes simplex virus receptor encoded by a nucleic acid that hybridizes with the sequence set forth in the Sequence Listing as SEQ ID NO: 1 under stringency conditions described herein.

The present invention also contemplates transgenic animals expressing a nucleic acid encoding a regulatory domain or a binding domain of a herpes simplex virus receptor, said nucleic acid comprising a fragment of the sequence set forth in the Sequence Listing as SEQ ID NO: 1. The uses contemplated for these transgenic animals can be, but are not limited to, methods to screen drugs, vaccines, or other compounds or substances for their anti-herpes simplex virus binding activity, or as a model animal which can be used to produce herpes simplex virus after being previously infected with HSV.

The nucleic acid used for generating a transgenic animal of the invention includes, but is not limited to, a cDNA fragment encoding a herpes simplex virus receptor or a binding domain of a herpes simplex virus receptor or a genomic sequence encoding a herpes simplex virus receptor or a binding domain of a herpes simplex virus receptor. ([See for methodology details, R. Ren et al., Transgenic mice expressing a human poliovirus receptor: a new model for poliomyelitis. *Cell* 63: 353–362 (1990)]. Such a genomic sequence may contain introns as well as exons, upstream and/or downstream regulatory sequences, and other functional and/or structural regions. Nucleic acids used for generating such a transgenic animal may be circular or linear molecules, and may be introduced into the animal with or without additional nucleic acids. Such additional nucleic acids include, but are not limited to, plasmid, phage, cosmid, viral, or mammalian cloning vectors, and the like. The nucleic acid may be introduced into a zygote or fertilized egg of a female animal containing two pronuclei, or embryonic stem cells prior to introducing the nucleic acid into an embryo, zygote, or fertilized egg of a female animal containing two pronuclei. The nucleic acid may be introduced into embryonic stem cells by transfection, retroviral infection, electroporation, injection, microinjection, and the like. After introduction of the foreign nucleic acid into the embryo, the embryo is transferred to the oviduct of a foster, pseudopregnant mother, and upon subsequent implantation into the uterus, the embryo may develop to term. Standard technical details of methods used to generate transgenic animals are discussed in detail by Hogan, et al., in "Manipulating the Mouse Embryo: A Laboratory Manual" (Cold Spring Harbor, N.Y.: Cold Spring Harbor Laboratory (1986)).

The transgenic animal of the present invention can be a mouse or a pig or other non-human animal selected for the presentation of characteristics sought to be altered and studied by infection with herpes simplex virus, or for practical reasons, such as ease of maintenance.

The transgenic animal of the invention can be used in a method of testing the efficacy of a herpes simplex virus vaccine of the invention. This method comprises administering the potential vaccine to a transgenic animal which expresses the introduced nucleic acid encoding a herpes simplex virus receptor or a binding domain of a herpes simplex virus receptor and determining whether the transgenic animal is protected from infection from herpes simplex virus. Protection of the transgenic animal from infection by herpes simplex virus may be determined in a number of ways, including, but not limited to, detecting the presence of virus in the serum, spinal fluid, plasma, blood, mucus, gastric fluids, feces, urine, and other fluids, neural tissue, testis, brain tissue, liver tissue, kidney tissue, heart tissue, lung tissue, placenta tissue, skin tissue, muscle tissue, pancreatic tissue, and other tissues. Detection of virus is contemplated to distinguish between detection of virus inoculum introduced into the animal and detection of replicating virus produced as a result of a failure of a potential vaccine to prevent infection. Methods of detection for the presence of replicating virus include, but are not limited to, PCR, ELISA, IFA, Southern blotting, Western blotting, Northern blotting, plaque assay, immunocytochemical techniques, and the like.

A transgenic animal of the invention can be used in a method of producing herpes simplex virus, comprising generating a transgenic animal expressing a foreign nucleic acid encoding a herpes simplex virus receptor or a binding domain of a herpes simplex virus receptor followed by productive infection of the animal with introduced herpes simplex virus. Herpes simplex virus replicated by cells that express the introduced foreign nucleic acid (HSV receptor activity) and become infected with herpes simplex virus can be harvested by any of a number of methods known to a skilled practitioner in the art. Harvesting the replicating herpes simplex virus from a transgenic animal expressing a herpes simplex virus receptor or a binding domain of a herpes simplex virus receptor may therefore provide a source of newly synthesized herpes simplex virus for other clinical (e.g., diagnostic) or research procedures, or for vaccines.

J. Vectors and Hosts

Vectors comprising the nucleic acids of the present invention is also provided. The vectors of the invention can be in a host capable of expressing the polypeptide fragments contemplated by the present invention. The present invention provides a vector comprising the nucleic acid set forth in the Sequence Listing as SEQ ID NO: 1. Additionally, the present invention provides a vector comprising a nucleic acid complementary to or capable of selectively hybridizing with the nucleic acid comprising the nucleotide sequences set forth in the Sequence Listing as SEQ ID NO: 1. An alternative coding sequence for the present receptor can also be expressed.

There are numerous *E. coli* expression vectors known to one of ordinary skill in the art useful for the expression of the antigen. Other microbial hosts suitable for use include bacilli, such as *Bacillus subtilis*, and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary an amino terminal methionine can be provided by insertion of a Met codon 5' and in-frame with the antigen. Also, the carboxy-terminal extension of the antigen can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carded out by yeast secretory systems. The Saccharomyces cerevisiae pre-pro-alpha-factor leader region (encoded by the MFα.- 1 gene) is routinely used to direct protein secretion from yeast (Brake et al., 1984). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage-signal sequence. The antigen coding sequence can be fused in-frame to the pre-pro-alpha-factor leader region.

This construct is then put under the control of a strong transcription promoter, such as the alcohol dehydrogenase I promoter or a glycolytic promoter. The antigen coding sequence is followed by a translation termination codon which is followed by transcription termination signals. Alternatively, the antigen coding sequences can be fused to a second protein coding sequence, such as Sj26 or β-galactosidase, used to facilitate purification of the fusion protein by affinity chromatography. The insertion of protease cleavage sites to separate the components of the fusion protein is applicable to constructs used for expression in yeast. Efficient post translational glycosolation and expression of recombinant proteins can also be achieved in Baculovirus systems.

Mammalian cells permit the expression of proteins in an environment that favors important post-translational modifications such as folding and cysteine pairing, addition of complex carbohydrate structures, and secretion of active protein. Vectors useful for the expression of active proteins in mammalian cells are characterized by insertion of the protein coding sequence between a strong viral promoter and a polyadenylation signal. The vectors can contain genes conferring neomycin resistance, hygromycin resistance, gentamicin resistance, or methotrexate resistance, or other genes or phenotypes suitable for use as selectable markers. The active polypeptide or polypepticle fragment coding sequence can be introduced into porcine cell lines using a zeomycin resistance-encoding vector, or a Chinese hamster ovary (CHO) cell line using a methotrexate resistance-encoding vector, or other cell lines using suitable selection markers. Presence of the vector RNA in transformed cells can be confirmed by Northern blot analysis and production of a cDNA or opposite strand RNA corresponding to the antigen coding sequence can be confirmed by Southern and Northern blot analysis, respectively. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from inununoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transformation is commonly utilized for prokaryotic cells, whereas calcium phosphate mediated transfection or electroporation may be used for other cellular hosts.

Alternative vectors for the expression of antigen in mammalian cells, those similar to those developed for the expression of human gamma-interferon, tissue plasminogen activator, clotting Factor VIII, hepatitis B virus surface antigen, protease Nexinl, and eosinophil major basic protein, can be employed. Further, the vector can include CMV promoter sequences and a polyadenylation signal available for expression of inserted nucleic acid in mammalian cells (such as COS-7).

The nucleic acid sequences can be expressed in hosts after the sequences have been operably linked to, i.e., positioned, to ensure the functioning of an expression control sequence. A suitable host would not express an endogenous herpes simplex virus receptor. These expression vectors are typically replicable in the host organisms either as episomes or as an integral part of the host chromosomal DNA. Commonly, expression vectors can contain selection markers, e.g., zeomycin resistance, tetracycline resistance or hygromycin resistance, to permit detection and/or selection of those cells transformed with the desired nucleic acid sequences (See, e.g., U.S. Pat. No. 4,704,362, incorporated herein by reference).

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

K. Purified Antibodies

A purified antibody that specifically binds the receptor or receptor fragments of the present invention, or homologs thereof is also provided. The antibodies can be polyclonal or monoclonal. The antibodies can specifically bind a unique epitope of the receptor. "Specifically bind" as used herein describes an antibody or other ligand that does not cross react substantially with any antigen other than the one specified, in this case, the HSV receptor of the present invention. Antibodies can be made by many well-known methods (see also, Harlow and Lane, Antibodies; A Laboratory Manual, Cold Spring Harbor Laboratory, Cold Spring Harbor, N.Y., (1988)). Briefly, purified virus or viral antigen can be injected into an animal and in intervals sufficient to elicit an immune response. Antibodies can either be purified directly, or spleen cells can be obtained fiom the animal. The cells are then fused with an immortal cell line and screened for antibody secretion. The antibodies can be used to screen nucleic acid clone libraries for cells secreting the antigen. Those positive clones can then be sequenced as described in the Examples or by other methods (see, for example, Kelly et al., Bio/Technology, 10: 163–167 (1992); Bebbington et al., Bio/Technology, 10: 169–175 (1992)).

The antibody can be bound to a substrate or labeled with a detectable moiety or both bound and labeled. The detectable moieties contemplated with the composition of the present invention can be those listed above in the description of the detection methods, including fluorescent, enzymatic and radioactive markers.

L. Vaccines

The virus receptor or viral receptor antigen, e.g., a purified antigenic polypeptide fragment encoded by the nucleic acids of this invention, can be used in the construction of a vaccine comprising an immunogenic amount of the virus receptor or antigen and a pharmaceutically acceptable carrier. The vaccine can be the entire antigen, the antigen on the intact receptor, *E. coli* or other strain, or an epitope specific to the antigen.

The vaccine can also be potentially cross-reactive with antibodies to other antigens. The vaccine can then be used in a method of preventing infection with the HSV described herein.

The purified polypeptide or fragments of the HSV receptor can be tested to determine their immunogenicity and specificity for use as a vaccine. Briefly, various concentrations of a putative immunogen are prepared and administered to an animal and the immunological response (e.g., the production of antibodies or cell mediated immunity) of an animal to each concentration is determined. Thereafter an animal so inoculated with the immunogen can be exposed to the virus to test the potential vaccine effect of the specific immunogenic fragment. The specificity of a putative immunogenic fragment can be ascertained by testing sera, other fluids or lymphocytes from the inoculated animal for cross reactivity with other closely related alphaherpes viruses.

Immunogenic amounts of the vaccine antigen can be determined using standard procedures. Briefly, various concentrations of a putative specific immunoreactive epitope are prepared, administered to a subject and the immunological response (e.g., the production of antibodies or cell mediated immunity) of the subject to each concentration is determined. The amounts of antigen administered depend on the subject, e.g., a human or a guinea pig, the condition of the subject, the size of the subject, etc.

Accordingly, therefore, the present invention provides a vaccine comprising the HSV receptor, an immunogenic polypeptide or fragments of the polypeptide. Examples of such polypeptides include those derived from a purified polypeptide encoded by the nucleotide sequences set forth in the Sequence Listing as SEQ ID NO: 1. Such a vaccine would naturally include immunogenic amounts of the virus receptor or polypeptide fragments and a pharmaceutically acceptable carrier.

The pharmaceutically acceptable carrier contemplated herein can comprise saline or other suitable carriers (Arnon, R. (Ed.) Synthetic Vaccines I: 83–92, CRC Press, Inc., Boca Raton, Fla., (1987)). By "pharmaceutically acceptable" is meant a material that is not biologically or otherwise undesirable, i.e., the material may be administered to an individual along with a selected compound without causing any undesirable biological effects or interacting in a deleterious manner with any of the other components of the pharmaceutical composition in which it is contained. The carrier will depend upon the method of administration and choice of adjuvant if one is used. An adjuvant can also be a part of the carrier of the vaccine, in which case it can be selected by standard criteria based on the antigen used, the mode of administration and the subject (Arnon, R. (Ed.), 1987). Methods of administration can be by the parenteral route, preferably by intramuscular or subcutaneous injection, depending on the particular vaccine used and the subject to whom it is administered. It can be appreciated from the above that the vaccine can be used as a prophylactic or a therapeutic modality. Thus, the invention contemplates methods of preventing or treating infection from herpes simplex virus and the associated diseases by administering the vaccine to a subject.

DETAILED DESCRIPTION OF SPECIFIC EMBODIMENTS

In the present invention, the combination of the novel porcine cell model system which is refractory to HSV entry, along with specific HSV B5 and/or HVEM receptor proteins enables the development of suitable assays for screening anti-viral agents and therapeutics. The assays of the present invention are useful for detecting the ability of agents to inhibit HSV entry or spread and provide for facile high-throughput screening of compounds suspected to be able to inhibit such entry (e.g., compound libraries, peptide libraries, and the like) to identify potential drug candidates.

In Vitro Screens to Identify Anti-Viral Agents or Therapeutics

One approach contemplated by the present invention is to look for small molecules i.e., biological or chemical compounds that specifically block HSV entry and replication. Blockage of attachment and penetration gives a specific target to prevent virus infection. However, it should be ensured that the development of these drugs, that interfere with interactions between cellular receptors and viral components, do not interfere with the normal function of the cellular molecule. HSV is one of many viruses that enter cells through direct interactions of the virus envelope with cell membrane. Development of such assays would depend upon the development of at least five. host-virus interaction systems, in order to establish controls for distinguishing specific versus non-specific blocking of HSV entry into porcine cell systems.

Molecules selected for testing/screening are added to a test system composed of (a) Uninfected transfected Porcine cells, (b) HSV infected B5 transfected cells, (c) HSV infected HVEM transfected cells, (d) HSV infected cells transfected with B5 and HVEM, (e) Untransfected Porcine cells as a control system.

Selected molecules are incubated in the test system for a period sufficient to permit HSV entry and replication. The various read-out systems which can be employed are as follows.

1. Determine if the Test Inhibitor Molecule Affects HSV Stable Binding in Porcine Cells A. Using Radiolabeled HSV Particles HSV virions were radiolabeled and purified as described. Roller bottles of HEp2 cells were inoculated with virus at 3–5 PFU/cell for 2 hr. After removal of inoculum, the cells were overlaid with medium 199 supplemented with 1% FBS, with or without [$^{35}$S]methionine (15 $\mu$Ci/ml) or [$^{3}$H] thymidine (20 $\mu$Ci/ml) and incubated at 37° C. for 48–72 hr. When the infected cells were labeled with [$^{35}$S]methionine, the medium 199 used had 20% of the normal levels of cold methionine. Virus was harvested and purified from infected-cell cytoplasmic lysates by centrifugation through dextran gradients (Dextran T10; Pharmacia LKB Biotechnology Inc., Piscataway, N.J.).

Infectious virus was quantitated by titrations on HEp-2 cells and radioactivity was quantitated by liquid scintillation counting. Particle numbers were determined by EM. Most virus preparations had titers of $10^8$ to $10^9$ PFU/ml. Particle/PFU ratios were usually ~50:1 for HSV-1 (KOS) and HSV-2 (333), and about 2-5:1 for HSV-1(F). Just before use, virus was diluted 1:4 (vol/vol) in PBS, centrifuged at 40,000 g for 1 hr., and resuspended in PBS.

Binding of Radiolabeled HSV to A 7 Cells Transfected With HSV Receptors:

For the binding experiments, the cells were plated either in 96-well round-bottomed plates (Gibco BRL, Gaithersburg, Md.), 24 well plates, or on the bottoms of the glass scintillation vials described above, and incubated at 37° C. overnight. The confluent monolayers were pretreated with PBS-BSA for 1 hr at 37° C. The cells were then washed three times with PBS-BSA and inoculated with the purified labeled virus in a sufficient volume of PBS-BSA to keep the cells covered with fluid.

The cells were exposed to the labeled virus in the presence or absence of drug candidate compounds for 6 hr at 4° C. on a shaker (pilot experiments revealed that 6 hr was required for the binding of virus to approach equilibrium), and the cells were then washed three times with cold PBS. If the cells had been plated on 96-well plates, they were transferred to scintillation vials after detachment with EDTA and scintillation fluid was added.

If the cells had been plated in the scintillation vials, then scintillation fluid was simply added for the quantitation of radioactivity bound to the cells. Results are expressed as number of virions bound per cell [ based on the specific activities of the virus preparations (virions per cpm)]. The degree of HSV binding in the presence or absence of drug compounds is quantitated.

B. FACS analysis of HSV binding

Approximately $1 \times 10^6$ (HSV receptor, B5 and/or HVEM) transfected-A7 cells in presence or absence of drug candidates are infected in suspension at 10 PFU/cell for 1 hr at 4° C. Test Viruses which can be used are dextran purified HSV-1(F), HSV-2(G), PRV(Rice), and HSV-1(FgD) made from Vero (without gD) and VD60 (with complemented gD) or HSV-1(SCgHZ) made from Vero (without gH) and F6 (with complemented gH) cells. Cells, on ice, are first washed with cold heparin (Sigma Co.) buffer (100(g) or PBS-A for 1 min. followed by two washes with cold PBS-A. Virus binding is assessed by analyses with fluorescence-activated cells sorter (FACS) after incubation for 30 min. at 4° C. with monoclonal antibodies (I-99-1 anti-gD, II-512 anti-gC, I-105 anti-gB) to HSV and polyclonal antibody to PRV viral glycoproteins. Anti-mouse or anti-rabbit IgG FITC conjugated antibody (Sigma Co.) is used as a fluorescence probe. Between each antibody incubation, cells are washed three times with cold PBS-A+1% BSA. FACS analyses is performed on FACScan from Becton and Dickinson using program Lysis II version 1.1. The degree of HSV binding in the presence or absence of drug compounds is quantitated.

2. Infection with HSV of the Transfected, Previously-Refractory Cells.

Infectivity Assays:

Infectivity assays were based on quantitation of β-galactosidase expressed from the viral genome. Adherent porcine A7 cells were plated in 96 well tissue culture dishes ($2-4 \times 10^4$ cells/well) in presence or absence of drug candidates at least 16 hr prior to infection. Cells were washed and exposed to virus (in 50 ul of phosphate-buffered saline [PBS] containing glucose and 1% calf serum [PBS-G-CS for 6 hr at 37° C. before solubilization in 100 ul of PBS containing 0.5% NP-40 and the β-galactosidase substrate, o-nitro-phenyl β-D-glucopyranoside (ONPG, 3 mg/ml). The reaction was monitored by spectrometry at several time-points after the addition on ONPG to define the interval over which the generation of product was linear with time (Dynatech ALICE reader or a spectromax 250).

Alternatively, HSV receptor transfected cells plated in 6 well tissue-culture dishes were exposed to virus in the presence or absence of drug candidates and infected cells visualized using the β-galactosidase substrate X-gal (GIBCO Laboratories), which yields an insoluble blue reaction product. After infection, washed cells were fixed (PBS containing 2% formaldehyde and 0.2% glutaraldehyde), permeabilized (2 mM $MgCl_2$ containing 0.01% deoxycholate and 0.02% NP-40), and incubated with buffered X-gal (0.5 mg/ml). Virus Yields from B5 and/or HVEM transfected cells that are infected with HSV-2, or HSV-1 in the presence of potential drug compounds, will be compared to yields from A7 cells transfected with virus alone, to determine the efficacy of the drug candidate.

EXPERIMENTAL

In the experimental disclosure which follows, the following abbreviations and methodology apply: g (gram); mg (milligrams); μg (microgram); M (molar); mM (milliMolar); μM (microMolar); nm (nanometers); L (liter); ml (milliliter); μl (microliters); ° C. (degrees Centigrade); m (meter); sec. (second); DNA (deoxyribonucleic acid); cDNA (complementary DNA); RNA (ribonucleic acid); mRNA (messenger ribonucleic acid); PAGE (polyacrylamide gel electrophoresis); BAP (6-benzyl aminopurine); Tris (tris (hydroxymethyl) -aminomethane); PBS (phosphate buffered saline); 2× SSC (0.3 M NaCl, 0.03 M $Na_3$citrate, pH 7.0); Gibco BRL (Gaithersburg, Md.); Sigma (St. Louis, Mo.).

Methodology

Cells and Viruses:

Chinese Hamster Ovary cells (CHO-K1), Human larynx epidermoid carcinoma (HEp-2) cells, African green monkey kidney (Vero) cells and human embryonic lung (HEL) cells were obtained from ATCC. The CHO-IEβ8 cell line was isolated after transfection of CHO-K1 cells with pMLPO1, a plasmid having the E. coli lacZ gene under control of the HSV-1 ICP4 promoter and expressing β-galactosidase upon infection of cells with HSV (M. L. Parish, R.I.M. and P.G.S., unpublished data). Except for Vero, all cells were grown in Dulbecco's modified medium (DMEM) (Gibco-BRL) supplemented with 5% or 8% fetal bovine serum (FBS, Hyclone). Vero cells for virus titration were grown in 199 medium with Hank's salts supplemented with 5% FBS or with 8% calf serum (CS, Hyclone).

Wild-type virus stains used were HSV-1(KOS), HSV-1 (HFEM), HSV-1(Patton), HSV-1(F) (Ejerico et al., 1968), HSV-1(SC16), HSV-1(17)and HSV-2(333). Mutant stains included KOS-rid1 and rid2. HSV-1(KOS)804 HSV-1(MP) and HSV-1(ANG) KOS-rid1-tk12 is a recombinant virus produced by inserting the E. coli lacZ gene driven by the HSV-1 ICP4 promoter in place of the thymidine kinase gene of KOS-rid1. These strains were propagated by passage on HEp-2 cells and titered on Vero cells. KOS-gL86, a mutant in which the E. coli lacZ gene with CMV promoter replaces part of the gL open reading frame, was propagated and titered on gL-expressing Vero cell transfectants. Mutant viruses obtained from these complementing cell lines were fully infectious for and expressed β-galactosidase in non-complementing cells but produced only noninfectious virus. HSV-1(F) was grown on HEp-2 cells and PRV (Rice) on SK6 cells. Mutant virus, HSV-1(SCgHZ) that lacks gH and expresses (β-galactosidase from the virus genome under the CMV immediate early promoter and supporter cell line F6. Mutant virus that lacks gD, HSV-1 FgD was grown on Vero-derived supporter cell line VD60.

Determination of Virus Yields and Infected Centers

Monolayers of cells were grown to confluency in either six well dishes or 25 $cm^2$ dishes and infected with HSV-1 or PRV for 90 min at 37° C. Infected cells were treated with citrate buffer, pH 3.0 for 1 minute to inactivate extracellular virus. The dishes were washed twice with phosphate buffered saline (PBS-A) and overlaid with DMEM containing 2.5% CS supplemented with penicillin and streptomycin (DMEV). Infected cells were incubated at 37° C. and harvested at the indicated time. Infectious yields were titered on Vero cells by using an overlay of 199 medium with Hank's salts supplemented with 2.5% CS and 0.5% methylcellulose (199V).

Infectious centers of HSV-1 were determined by exposing $3 \times 10^6$ cells to virus at 3.0 PFU/cell. After 90 min of infection, virus inoculum was removed and monolayers washed with citrate buffer and PBS-A as described above. At 3 hrs post-infection cells were detached with trypsin and diluted in PBS-A containing 2.5% CS. Infectious centers were determined in duplicate on Vero cell monolayers overlaid with 199V. Cells were stained at 48 hrs with Giemsa and infectious centers determined by counting plaques.

Polyethylene Glycol (PEG) Treatment of HSV

Cell monolayers were infected with HSV-1 at 2.0 PFU/cell for 1 hr at 37° (C. Virus inoculum was removed and monolayers treated with citrate buffer and PBS-A. The monolayers were exposed to 50% (wt/vol.) PEG 6000 and sequentially washed with 1:3 and 1:7 dilutions of PEG. Cells were washed twice with DMEM and overlaid with DMEV until plaques were evident.

Southern Blot of Viral DNA

Confluent monolayers in 12 well dishes were infected with HSV-1(F) at 10 PFU/cell and total DNA isolated at 7 or 24 hr. post-infection. Equal amounts of DNA, determined by O.D. measurement at 260 nm, were digested with EcoR-1 (Gibco-BRL), run on a 0.8% agarose gel and transferred to a nylon membrane by an alkaline turbo blotter (Schleicher and Schuell). HSV-1 DNA was detected with a $^{32}p$ gD-1 probe. The membrane was washed and autoradiograms obtained by exposing the membrane at $-80°$ C. to Hyperfilm (Amersham) with an intensifying screen.

FACS Analysis of HSV Binding

Approximately $1 \times 10^6$ HEL or A7 cells were infected in suspension at 10 PFU/cell for 1 hr at 4° C. Viruses used were dextran purified HSV-1(F)[ATCC VR-733], HSV-2(G) [ATCC VR-734], PRV(Rice), and HSV-1(FgD$\beta$) made from Vero (without gD) and VD60 (with complemented gD) or HSV-1(SCgHZ) made from Vero (without gH) and F6 (with complemented gH) cells. Cells, on ice, were washed with cold heparin (Sigma Co. St. Louis, Mo.) buffer or PBS-A for 1 min. followed by two washes with cold PBS-A. Virus binding was assessed by analyses with fluorescence-activated cells sorter (FACS) after incubation for 30 min. at 4° C. with monoclonal antibodies (I-99-1 anti-gD, II-512 anti-gC, I-105 anti-gB) to HSV and polyclonal antibody to PRV viral glycoproteins. Anti-mouse or anti-rabbit IgG FITC conjugated antibody (Sigma Co.) was used as a fluorescence probe. Between each antibody incubation, cells were washed three times with cold PBS-A+1% BSA. FACS analyses were performed on FACScan from Becton and Dickinson using program Lysis II version 1.1.

Plasmid Constructs

The B5 cDNA of 1.2 kb has been subcloned out of the original vector into pCDNA3.1/zeo/CAT that contains a zeocin resistant gene. It also has been subcloned into pCDNA3/myc plasmid to express a myc epitope tagged protein. These plasmids have been tested by transient transfection into A7 cells and they contain the sequence needed to confer susceptibility to HSV. A7 cells have been transfected and are under zeocin drug selection for stable B5 expressing A7 cell clones.

Construction of Stably Transformed Porcine Cells that Express B5

Porcine cell lines that stably express B5, enable the function of B5 in the absence of other human products that may be involved in entry. With stably transformed cell lines the effect of B5 on HSV entry was exploited. Methods:

The pCDNA3.1/ZEO/CAT-B5 plasmid was transfected into low passage A7 cells and cells are selected for resistant to zeocin. Colonies were picked, cell lines isolated in 24 well plates and tested for β-galactosidase expression from entry of HSV(ICP4) lacZ+. Positive cell lines were expanded and tested for production of HSV-1 yields compared to vector only transfected A7, HB19 (A7 cells that stably express HVEM) and HEp-2 cells. B5 cell lines with a range of susceptibility to HSV were chosen for further studies of B5 RNA expression and protein levels, both total and cell surface as determined by Western blots and FACS analysis, respectively. Protein expression was detected using an antibody to B5 as described above. Growth curves indicated cell stability, and also that B5 had no effect on A7 cell morphology or growth rates. Production of B5 stable porcine cell lines also indicated that the human gene product is not toxic to porcine cells even if expressed in high levels as can occur under control of the CMV IE promoter. Analysis of RNA and protein levels determined that cells with a range of B5 levels were isolated. The morphology and growth properties of HVEM stable transformed cell lines also did not differ obviously from vector only or parental cells even though they were fully susceptible to HSV-1 and HSV-2.

Production of Polyclonal, and Monoclonal, Antibodies to the B5 Gene Product Using an Epitope Tagged Gene Construct or Synthetic Peptides.

Methods

Myc tagged B5 were expressed in porcine cells and affinity colunm chromatography was used with anti-myc antiobodies to purify tagged B5 from cell lysates. T]he purified material was tested for purity by SDS-PAGE and digested with the appropriate protease to remove the myc tag, while keeping as much as possible of the B5 protein. Modification of the initial expression vector allowed insertion of sequences encoding amino acids that served as a convenient site for specific proteases that have no, or few cleavage, sites in the B5 protein. B5 fragments were purified by size exclusion chromatography, mixed with Hunter's adjuvant and injected as immunogens for rabbits. Alternatively, if the myc tag is difficult to be removed, the entire molecule can be injected and serum preadsorbed with myc protein. For antibodies against HVEM, peptides of HVEM were synthesized as 15–21 amino acids linked to a lysine carrier, and these were used in Hunter's adjuvant to immunize rabbits. Serum titers were checked for positivity for HVEM peptides by ALICE. For B5, based on Jameson-Wolf analysis which predicts potential antigenic determinants by valuing hydrophilicity, surface probabilities, backbone flexibility and the secondary structure of the protein, suitable peptides were chosen. These peptides were used individually or in combination to immunize rabbits.

Rabbits inoculated every 28 days were bled 10–14 days after inoculation and serum tested in ALICE against the antigen used for immunization, i.e., B5 fragments, synthetic peptides or myc tagged intact protein. Positive serum were tested against B5 expressing cells in FACS to determine if it recognized the native B5 protein and by immunoprecipitation in a Western blot to determine if it recognized denatured B5. Anti-B5 sera were also tested for inhibition of HSV infection in porcine, HEp-2 and Vero cells.

HVEM:

Fc Production, Characterization, and Use as Immunogen

HVEM:Fc secreted into the medium of pBL58-transfected CHO-K1cells was purified by Protein G-Sepharose chromatography. HVEM:Fc was denatured by boiling for 5 min in 0.5% SDS, 1% B-mercaptoethanol, and carbohydrate modifications determined by incubating overnight at 37° C. with endo F (200 mU, 1% NP-40, 50 mM sodium phosphate [pH 7.5]) or endo H (1 mU, 50 mM sodium citrate [pH 5.5]).

Alternatively, samples were digested overnight at 37° C. with neuraminidase (4 mU, 50 mM sodium citrate [pH 4.5]), then denatured and incubated overnight at 37° C. with endo F (200 mU) and 0-glycosidase (0.5 mU) in 1% NP-40, 50 mM sodium phosphate (pH 7.5). Western blots of control and glycosidase-treated samples were probed with a mixture of anti-rabbit 1gG peroxidase conjugates (GibcoBRL 9814SA and Sigma A6667) at concentrations of 1:1000 in BLOTTO (10 mM Tris [pH 7.4], 150 mM NaCl, 5% powered milk, 0.05% Tween-20), followed by chemiluminescent detection with ECL reagent and Hyperfilf-MP (Amersham).

Rabbit polyclonal antibodies were produced by subcutaneous injection purified HVEM:Fc mixed with Hunter's TiterMax adjuvant at Pocono Farms, Inc. For immunoprecipitation, lysates were prepared with 1% Triton X-100 in 150 mM NaCl, 20 mM Tris-HCl (pH 8.0), containing protease inhibitors (2 ug/ml of aprotinin; 2 ug/ml of leupeptin; 1 ug/ml of pepstatin A; 5 mM phenylmethylsulfonyl flouride) and mixed on ice with rabbit preimmune or immune serum (10 ul/200 ul of lysate).

Samples of cell lysates and immunoprecipitates collected on Protein A-agarose were subjected to SDS-polyacrylamide gel electrophoresis and transferred to nitrocellulose membranes. The membranes were incubated in BLOTTO for 1 hr of blocking and then with the anti-hemagglutinin antibody 12CA5 (Wilson et al., 1984) diluted 1:5000 in BLOTTO, followed by horseradish peroxidase-coupled goat anti-mouse 1gG (Boehringer Mannheim) diluted 1:10,000. Detection of second antibody was by incubation in ECL reagent and exposure to Amersham Hyperfilm-MP (Amersham).

EXAMPLE 1

In this example, experiments have been described that led to the isolation of a homogeneous porcine cell line, A7, that is blocked at HSV entry (although contains heparan sulfate), but is competent to support other events in HSV replication.
Isolation of SK6 Clonal Cell Line Infectious yields of both HSV serotypes from ST cells were three to four orders of magnitude lower than yields from human HEp-2 and HEL cell lines. Exposure to an HSV-1(ICP4$^-$) mutant virus, defective in viral replication and spread, which expresses β-galactosidase indicated that less than 1% of cells in ST or SK6 monolayers were susceptible to HSV-1 infection. Clonal cell lines, were isolated by limiting dilution, from ST and SK6 cell lines and the susceptibility of the clones to HSV infection were determined. SK6 cell clones were stable and were easily propagated while ST clones were not stable.

Relative to HEp-2 cells, all 30 of the SK6 cell clones isolated were poorly susceptible to HSV. All retained the ability to replicate pseudorabies virus (PRV), an alphaherpesvirus that naturally infects swine, to the expected titers ($10^5$–$10^6$ PFU/ml from $1 \times 10^6$ cells) after 10 hr. infection at 0.01 PFU/cell. This indicated that the clones were not altered to with regard to susceptibility to PRV infection. Infectious HSV yields from the isolated SK6 clones ranged from low (<10% of yields from parental SK6) to high (>100%). Two cell clones SK6-A7 (A7) and SK6-E1 (E1) were selected for further characterization because of their respective low and high susceptibility to HSV-1 compared to parental SK6 cells. Their amount and types of HS were not significantly different than for HEp-2, Vero or ST cells.

A time course of HSV-1 yields showed efficient virus infection and spread in HEp-2 cells to produce high titers ($10^8$ PFU/ml from $1 \times 10^6$ cells) after 36 hr. of infection. In contrast, for parental SK6 and both clones, HSV titers were reduced. Yields over time from A7 cells were consistently up to six orders of magnitude lower than those from HEp-2 cells and five fold lower than parental cells. Virus yields from E1 cells, compared to parental cells, were significantly higher over time to produce a 29 fold increase in HSV-1 titers. The susceptibility range for clonal porcine cell lines was consistent with heterogeneity previously predicted by infection with HSV-1(ICP4$^-$) lacZ indicator virus. More susceptible cells in the parental population, like the E1 clone, produced the virus yields observed from the parental SK6 population. Most of the parental SK6 cells, and most of the resulting clones, did not stain positive for β-galactosidase production from the ICP4 mutant virus and were poorly susceptible to HSV infection.
Characterization of SK6 Clonal Cell Lines Next, it was determined by infectious centers, if the HSV-1 yields from A7 and E1 cell clones, were due to differences in the number of cells that become infected. In monolayers containing $3 \times 10^6$ cells, for parental SK6, $5 \times 10^3$ individual cells became infected compared to five fold fewer infected cell centers with monolayers of A7 cells. The relative number of infected cells correlated with the yields from SK6 and A7 monolayers. However, the number of individual E1 cells that were susceptible to HSV-1 infection were not higher than, nor significantly different from the parental cell line. Since virus yields were 29 fold higher for E1 cell monolayers, it was apparent that mechanism(s) other than an increase in the number of infected cells accounted for higher yields from E1.

After entry, HSV genes are transactivated, viral proteins are made and host protein synthesis is inhibited. Protein profiles of SK6, A7 and E1 compared to HEp-2 cells exposed to HSV-1(F) showed that there were no viral proteins or shut-off of host protein synthesis in parental or clonal porcine cells. At 40 PFU of input virus per cell, evidence of virus infection was detected only in susceptible HEp-2 cells. Even when SK6, A7 and E1 cells were exposed to HSV-1 at 400 PFU per cell, there was no evidence of virus protein synthesis or host shutoff.

HSV interaction with clonal porcine cells also was examined by southern blot analyses of total cellular DNA to monitor viral DNA replication. At seven hrs post infection, a low amount of, or no DNA, was detected in SK6 parental or A7 or E1 cells. By 24 hrs post infection after viral DNA was amplified by several rounds of replication. HSV DNA increased in the parental and E1 monolayers, but was still barely detectable in A7 cells. Relative levels of viral DNA detected in porcine cells was consistent with poor titers, low staining with indicator virus, few infected cell centers and absence of viral protein synthesis, and indicated that HSV does not initiate gene expression.

Polyethylene glycol (PEG) mediated viral fusion was used to confirm an entry defect and to determine if the SK6 clonal cells were defective only at HSV-1 entry. PEG treatment significantly increased the number of infectious centers 1000 fold with parental and clonal SK6 cells compared to untreated controls. There was only marginal (<10 fold) increase in the number of infectious centers with highly susceptible HEp-2 cells. As described for ST cells, HSV can replicate in SK6 parental and clonal cells if entry is bypassed. That the number of infectious centers for porcine cells were comparable to those of HEp-2 cells after PEG treatment indicated that low susceptibility of porcine cells was due to a block only at virus entry. This example shows that a homogeneous porcine cell line, A7, was isolated that was blocked at HSV entry and contained HS, but was competent to support other events in HSV replication.

EXAMPLE 2

Figure 2:
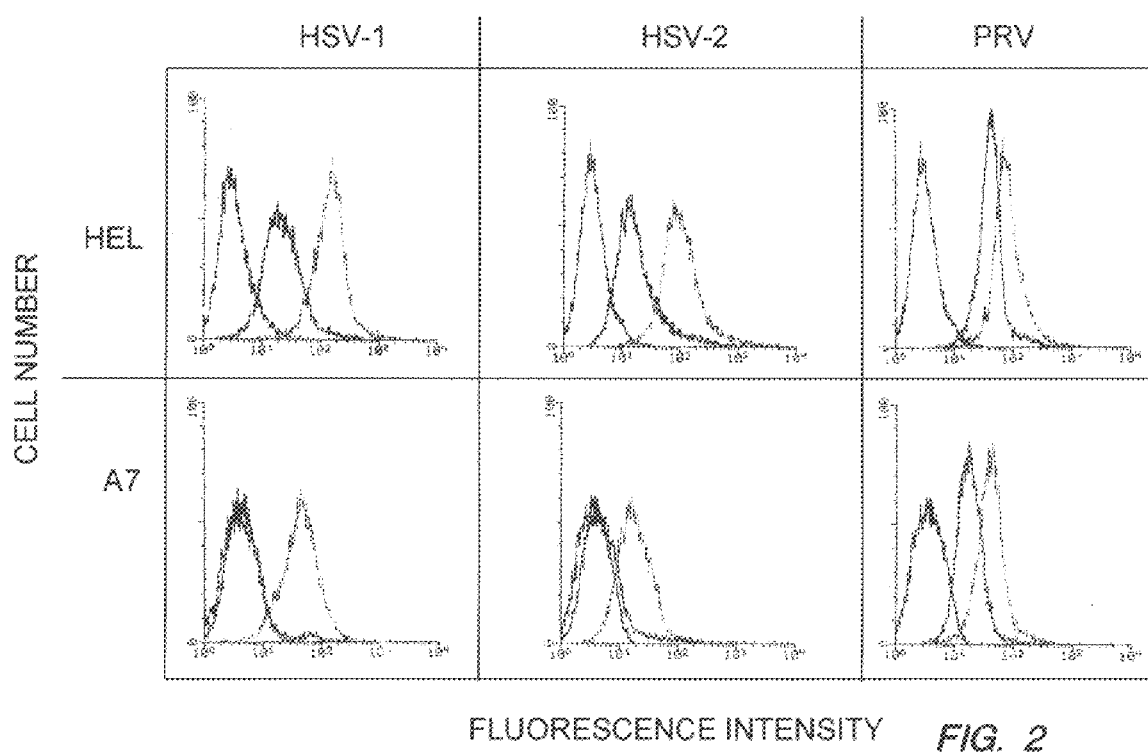
FIG. 2 shows HSV binding to HEL and SK6-A7 cells by FACS analysis.

In this example, HSV binding to the above mentioned HEL and A7 cells is demonstrated (See FIG. 2). A7 cells has functional levels and types of HS, but appeared to lack a functional non-HS receptor(s) that is essential for HSV entry. These cells were used to explore binding of HSV to cell surface receptors that leads to penetration and viral replication. Attachment of HSV-1, HSV-2, PRV and HSV-1 null viruses to A7 and HEL cells was examined under conditions previously shown to differentiate entry events. Cells at 4° C. were exposed to purified wild type or null viruses grown to contain or lack the indicated glycoprotein. The amount of virus binding that was sensitive, or resistant, to heparin elution was determined to distinguish two types of HSV or PRV attachment: initial, heparin-sensitive, and stable, heparin-resistant binding as previously defined for HSV and PRV infection. Total cell-associited virus after PBS-A wash included virus that was bound to cells through heparan sulfate or through other receptors. Virus that remained cell associated after washing with heparin buffer was defined as stably attached and is likely bound through multiple HS interactions or by binding to non-HS receptor (s). High levels of both HSV-1(F) and HSV-2(333) bound to highly susceptible HEL cells. Approximately 50% of total bound virus could be removed with heparin wash while the remaining virus was cell associated and resistant to heparin wash. Less total HSV bound to A7 cells that contained HS, but lacked a functional non-HS receptor. HSV binding to A7 cells was completely removed with heparin wash to indicate lack of stable attachment. High levels of PRV bound to HEL and A7 cells with profiles representative of both HS dependent and independent interactions. In this example, the data indicated that HSV attachment that leads to entry occurs through at least two clearly discernible phases that can be distinguished by differential wash and FACS analyses. A cell surface component needed for HSV stable attachment is present on HEL cells, and missing or not functional on A7 cells.

HSV Components for Stable Binding

To explore the virion components involved in stable attachment, FACS binding analyses were performed with purified HSV-1(FgD) or HSV-1(SCgHZ) null mutant virus that could be grown to contain or lack gD or gH. Previous findings have implicated an essential role for these virion glycoproteins in HSV stable attachment or penetration. Complemented infectious mutant virus grown to contain gD bound to HEL cells at levels similar to wild type virus. In comparison, for these cells, total binding was substantially lower for uncomplemented noninfectious gD null virus. The wash with heparin completely removed the gD null virus that bound to HEL cells. For poorly susceptible A7 cells, heparin resistant stable virus binding did not occur whether viruses were grown to contain, or lack, gD in the their envelope. A7 cells lacked a functional receptor for HSV stable binding such that presence or absence of gD in the virion made no difference in attachment profiles.

Next, binding of virus grown to contain, or lack gH, another essential HSV glycoprotein implicated in entry was examined. On HEL cells, stable binding was evident whether virus contained or lacked gH. However, no stable binding was detectable on A7 cells for either virus. These results demonstrated that stable binding characteristic of efficient HSV infection and entry, requires gD, but not gH in the virion envelope. FACS binding profiles were similar with these viruses for HEp-2 or Vero cells. This example shows that, presence of a non-HS receptor on the cell and of gD in the virion were needed to mediate stable binding that eventually leads to HSV entry. Lack of either the non-HS cellular receptor, as on A7 cells, or gD in the virus as with the gD null virus, impaired an essential function in HSV binding that leads to penetration. Also, the receptor(s) that are absent, or not functional, for parental or clonal SK6 cells, are involved in stable attachment through interactions directly, or indirectly with gD.

EXAMPLE 3

In this example, experiments have been described that demonstrate the role of viral glycoproteins for HSV entry. HSV Entry by Direct fusion Involves a Cascade of Multiple Binding Events:

Previous studies indicate HSV can enter cells by fusing with the plasma membrane and does not require pH change. In the present example, different roles for essential glycoproteins D (gD) and gH, both implicated in HSV entry at penetration, were demonstrated with viruses neutralized by anti-gD or anti-gH monoclonal antibody. Saturation blocking of Vero cells and of Hep-2 cells indicated that presence of gD and likely gH, but not gC or gB, in the virion was important for saturable HSV binding to cells. Saturation of cells with UV inactivated virus to block entry of challenge virus did not saturate HS. This indicated that non-HS receptors existed and were limited for infection. Also, HSV-1 and HSV-2 used a common non-HS receptor for entry into cells from the native host, Hep-2 and also into highly susceptible Vero cells. Lack of complete cross blocking of one by the other indicated that the HSV serotypes did not use identical receptors. This was consistent with previous reports that same or different receptors may be used by HSV 1 and HSV 2. In the multiple attachments for entry, both viruses may bind a common component, and also to components that maybe different.

Using another experimental approach to explore the events in HSV entry, kinetics of HSV binding and penetration established that at least two types of attachment can be distinguished experimentally (See FIG. 1). "Initial attachment" occurs for virus that resists PBS elution, but is sensitive to heparin elution. "Stable attachment" occurs for virus that resists heparin elution, but is sensitive to extracellular inactivation by low pH buffer since the virus is not yet protected by penetration into the lipid membrane. Kinetics of these attachment steps vary for the same inoculum of HSV-1 when exposed to highly susceptible Hep-2 or Vero cells. These results indicated that entry is a multi-step process involving multiple receptors that are distributed differently for Vero and HEp-2 cells.

In contrast to HEp-2 and Vero cells, poorly susceptible swine testis (ST) and swine kidney (SK-6) cells were defective in HSV entry, but allowed initial attachment to HS. There was no stable attachment of HSV on these cells and hence no penetration or infection. By FACS analysis (See FIG. 2), porcine cells were defective for stable attachment of HSV 1 and HSV 2, but showed both initial and stable attachment for PRV. Experiments with null mutant viruses showed that gD, but not gH was required in the virion envelope to mediate HSV stable attachment. The experimental results and accumulated information available in the field strongly supported a proposed model (See FIG. 1) for HSV entry, which is similar to that proposed with other viruses, that multiple attachments to HS and other non-HS cell surface molecules trigger a membrane fusion event. By FACS analysis and using gD null virus, it was confirmed that gD in the virion is essential for entry. Further, it was found that gD is required at stable attachment prior to penetration. gD is hypothesized to interact with gH to modulate or trigger gH-mediated membrane fusion. Glycoprotein H functions were previously postulated to occur subsequent to, or in conjunction with, but not before gD functions in HSV entry. It is believed, a stable attachment receptor(s) is essential for HSV entry and is missing, or not functional on porcine cells. These receptor(s) may be a single protein or homogeneous multimer thereof, or it may be composed of a complex of different cellular proteins. The functional stable attachment receptor or a component in a complex could vary on susceptible cells from different species (e.g., monkey or human) or for different cell types (neuronal vs. non-neuronal).

Next, to examine the roles of HS and putative non-HS receptors, human Hep-2 and HEL cells, monkey VERO cells and porcine SK-6 or ST cells were used. Susceptible HEp-2, HEL and Vero cells undersulfated by over 80% due to presence of sodium chlorate still allowed entry and replication of HSV to levels much greater than fully sulfated porcine cells. In this example, experimental findings and results with mouse cells defective in HS, or CHO mutant cells indicated that heparan sulfate is not required for HSV entry. Although HS seems to enhance the efficiency of infection, infection occurred when it is missing or under-sulfated. It is likely that initial binding of HSV to HS associates the virus with the cell to increase probability of binding to cell components that mediate stable attachment required for penetration.

EXAMPLE 4

Figure 3:
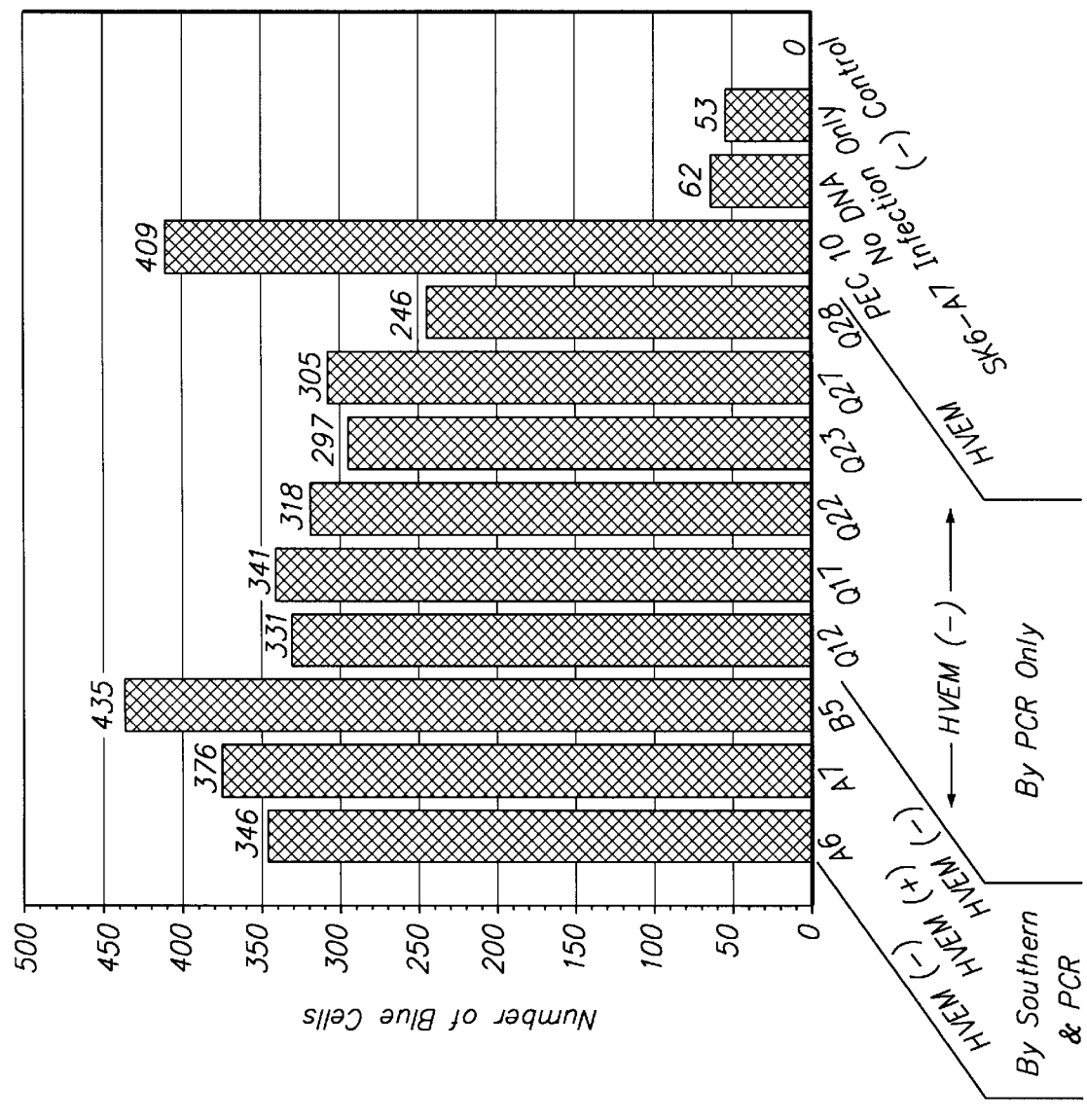
FIG. 3 is a graph which shows transfer of HSV susceptibility to A7 cells by human cDNAs.

In this example, cloning experiments of human cDNAs that confer susceptibility to HSV are described (See FIG. 3). A clonal porcine kidney cell line, SK6-A7 (A7) as recipient cells were used to screen a human cDNA library for clones that confer susceptibility to HSV. A7 cells produced $10^6$ fold lower HSV yields than HEp-2 cells and five fold lower than parental SK-6 cells. They support HSV replication when viral DNA is transfected or virus entry is mediated by PEG. For receptor cloning, cells were transfected with the purified plasmids, subsequently infected with HSV-1 (ICP4-) lacZ and stained for β-galactosidase expression from the lacZ in the viral genome. By matrix cloning of cDNA's batches that progressively decreased in number to individual purified plasmids, cDNA's were isolated that increased HSV infectivity into A7 cells. PCR and Southern hybridization analyses defined clones that were positive or negative for HVEM. The HVEM negative clones were selected for B5. This example shows the isolation of cDNA clones that confer susceptibility to HSV.

EXAMPLE 5

Figure 7:
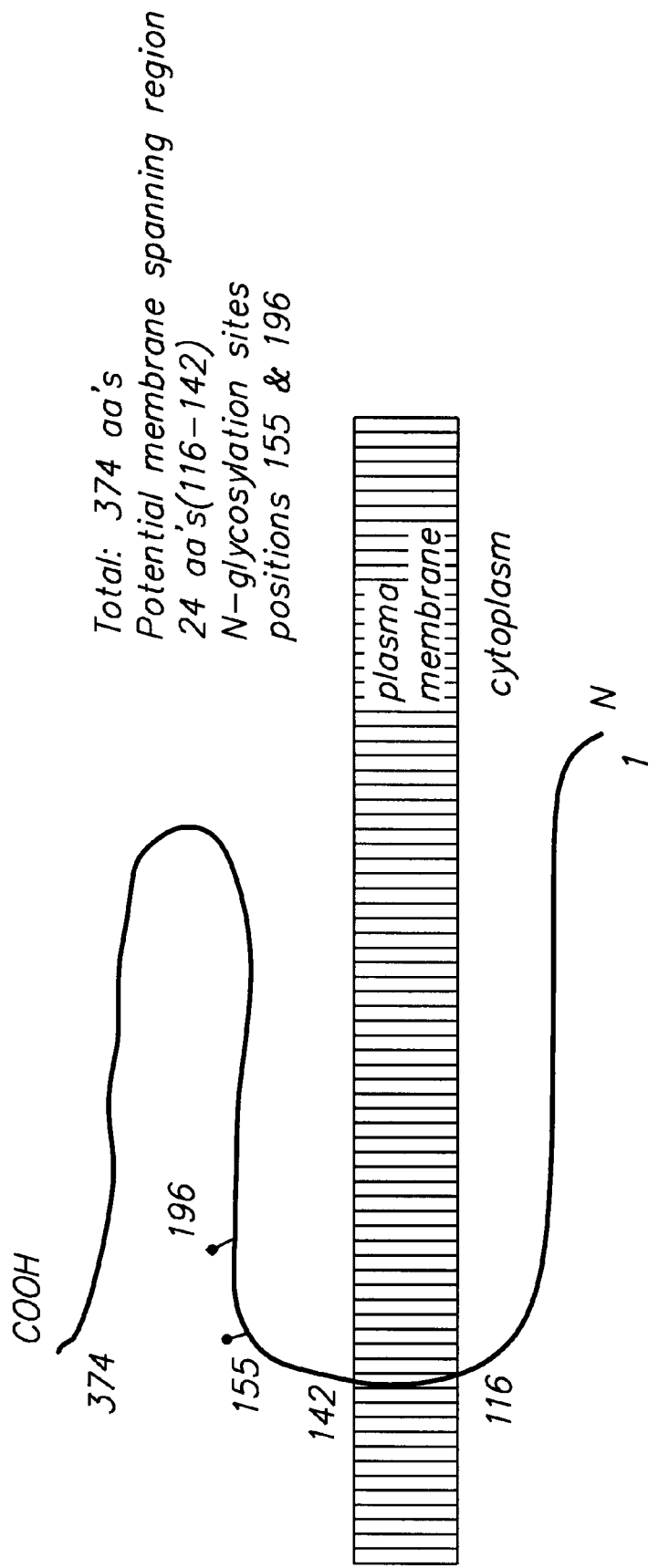
FIG. 7 shows a schematic of the predicted B5T74 protein.
Figure 8:
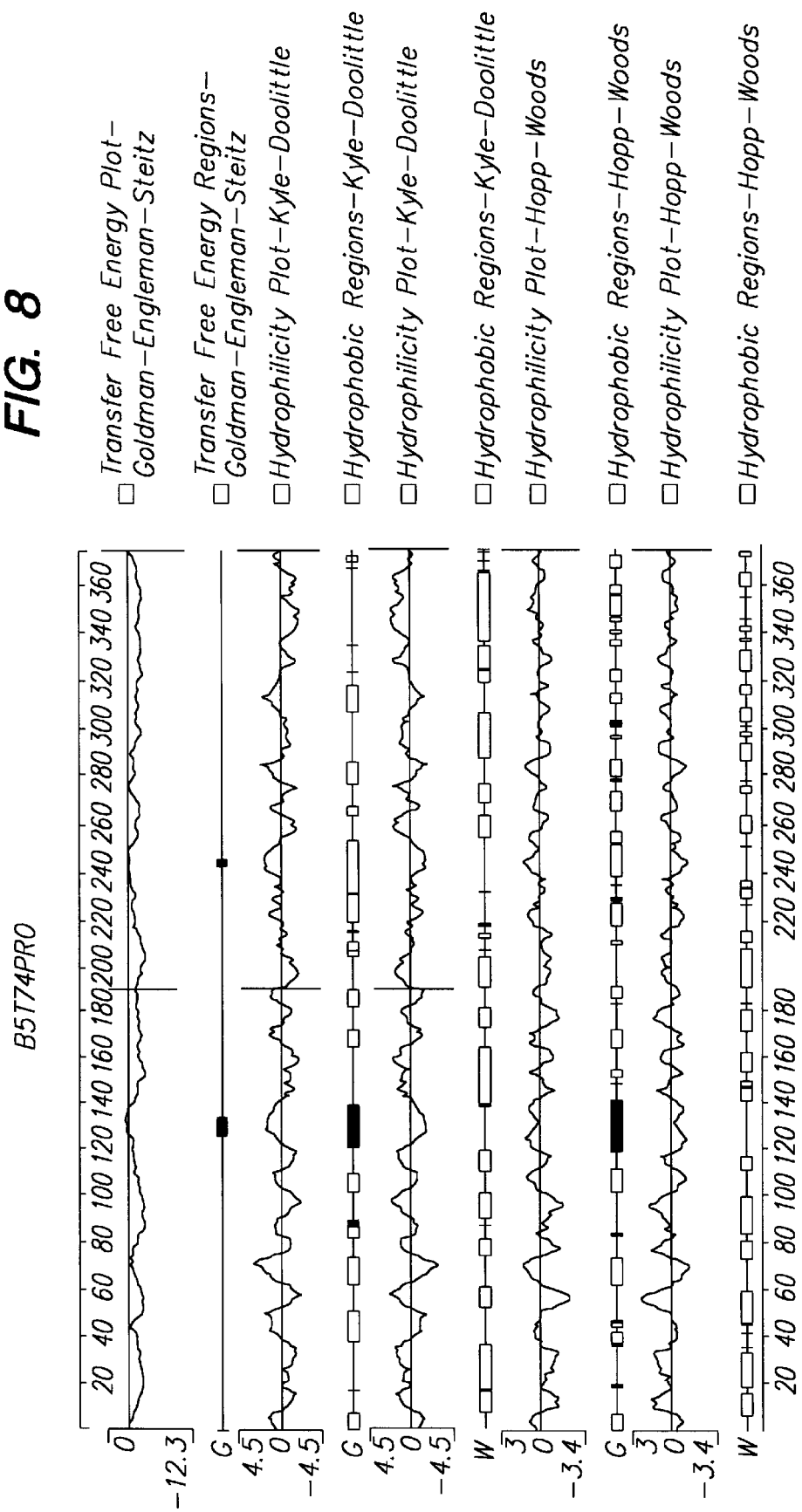
FIG. 8 shows hydrophobicity/hydophilicity plots of the predicted B5T74 protein. The computer programs used for the plot are indicated on the right.
Figure 10B:
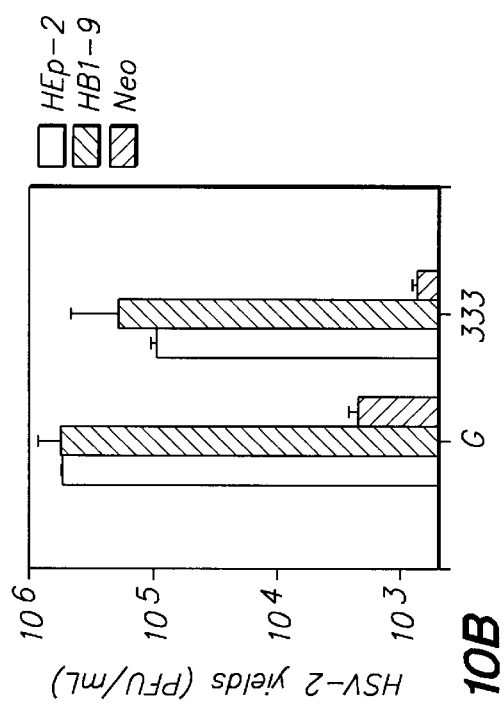
FIGS. 10A, 10B, 10C and 10D are bar graphs which show the yields of HSV-1 and HSV-2 from cells expressing HVEM. Infectious yields from strains of HSV-1 (A,C) or HSV-2 (B,D) virus are shown from HEp-2 cells. HB1-9 (HVEM expressing porcine cells) and Neo (porcine cells transformed with the vector only).
Figure 10D:
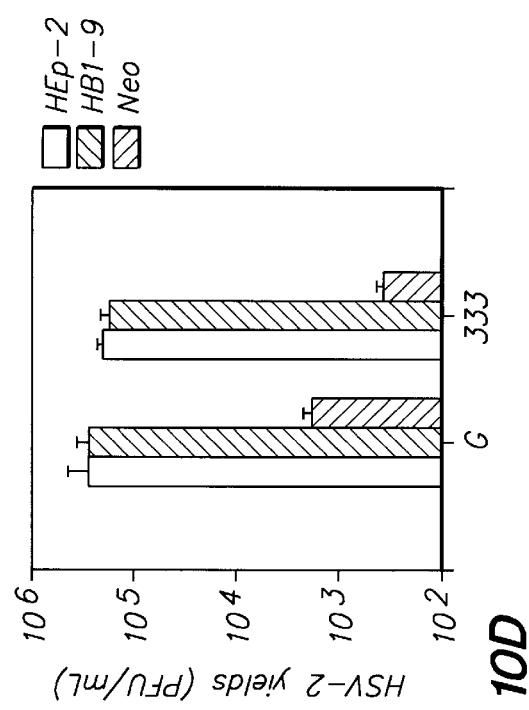
Figure 10A:
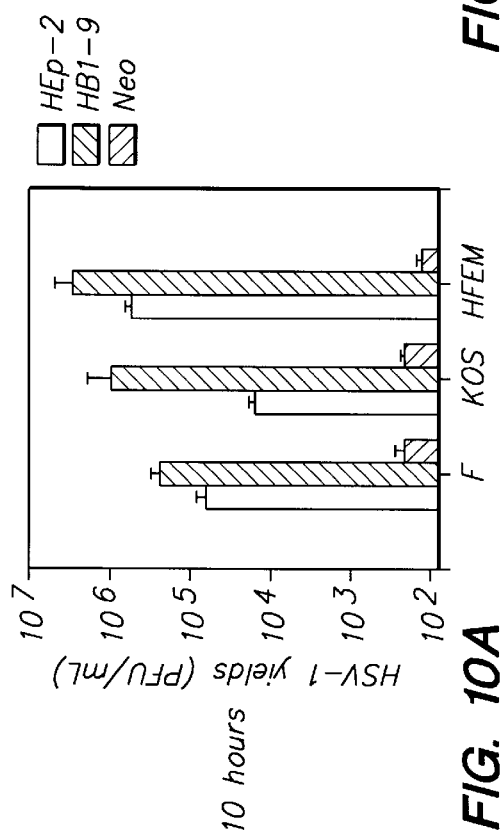
Figure 10C:
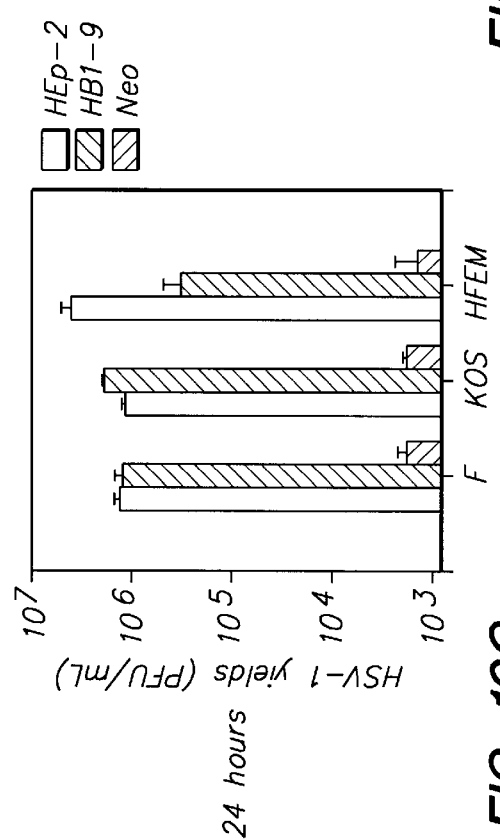

This example describes the Sequencing and computer analyses of B5. FIG. 3 shows the level of transfer of susceptibility as a number of blue foci containing single or multiple blue cells after infection by HSV-1 (ICP4-) lacZ. In several independent experiments, transfection of the B5 clone resulted in blue foci equal to or greater than HVEM (A7 or pBEC10). pBEC10 is a plasmid that contains the nucleic and encoding the HVEM receptor. See FIG. 4 for the nucleotide sequence SEQ ID NO: 3 of HVEM in the 10 clone. Nucleotide sequencing of both strands of the 1288 nucleotides of the B5T74 (B5) cDNA insert revealed an open reading frame from nucleotide 80–1204(See FIG. 5 SEQ ID NO:1). It encoded a predicted protein with 374 amino acids and molecular weight of approximately 42,500 daltons (See FIG. 6 SEQ ID NO:2). A strong Kozak's consensus sequence surrounded the start codon and a classical polyadenylation tail after the stop codon. Hydrophilicity plots by the analysis of Kyte-Doolittle, Hopp-Woods or Goldman-Engleman-Steitz of the predicted amino acid sequence revealed presence of a possible membrane spanning domain, and potential glycosylation sites only on one side of the putative transmembrane domain (See FIG. 7, FIG. 8). However, a typical cleavable signal peptide at the N-terminus of B5 was not located. Clustal method pairwise sequence alignment of the predicted B5 amino acid sequence with known members of the TNFα receptor family and HVEM indicated that B5 is not a member of this family (See FIG. 9A). Neither the overall structure nor alignment of conserved cysteine residues fitted with HVEM or family members. Sequence pair distance and phylogenetic analyses also indicated no relationship of the B5 protein to HVEM, CD30, CD40 or HFAS (See FIG. 9B). There was no identity with genes or proteins in the EMBL or Swiss-Prot databases. Highest homologies are with other human membrane proteins that may play a role in signaling at cellular membranes. In this example, B5 is shown to be a novel human gene encoding a predicted protein that is clearly distinct from HVEM and appears to be a type II membrane spanning, cell surface protein.

EXAMPLE 6

In this example, experiments are described that determine the functions of HVEM.

Functions of HVEM: Many of the cDNAs that transfered susceptibility for HSV to porcine cells contained the HVEM coding sequence. To explore the affect of HVEM on porcine cells, the nucleic acid encoding the HVEM (See FIG. 4 SEQ ID NOS: 3–4) (pBEC10) was transfected using the vector pBEC10 into A7 cells to make stable HVEM expressing cell lines. Of over 37 cell lines isolated, eight were characterized for growth properties and susceptibility to HSV infection. All were stable for growth and showed no unusual morphological changes from parental A7, SK-6 or vector only transformed cells (Neo). One of the most susceptible to HSV-1(lacZ) infection was called HB1–9. This was examined for interactions with HSV, and the results summarized below.

Figure 11:
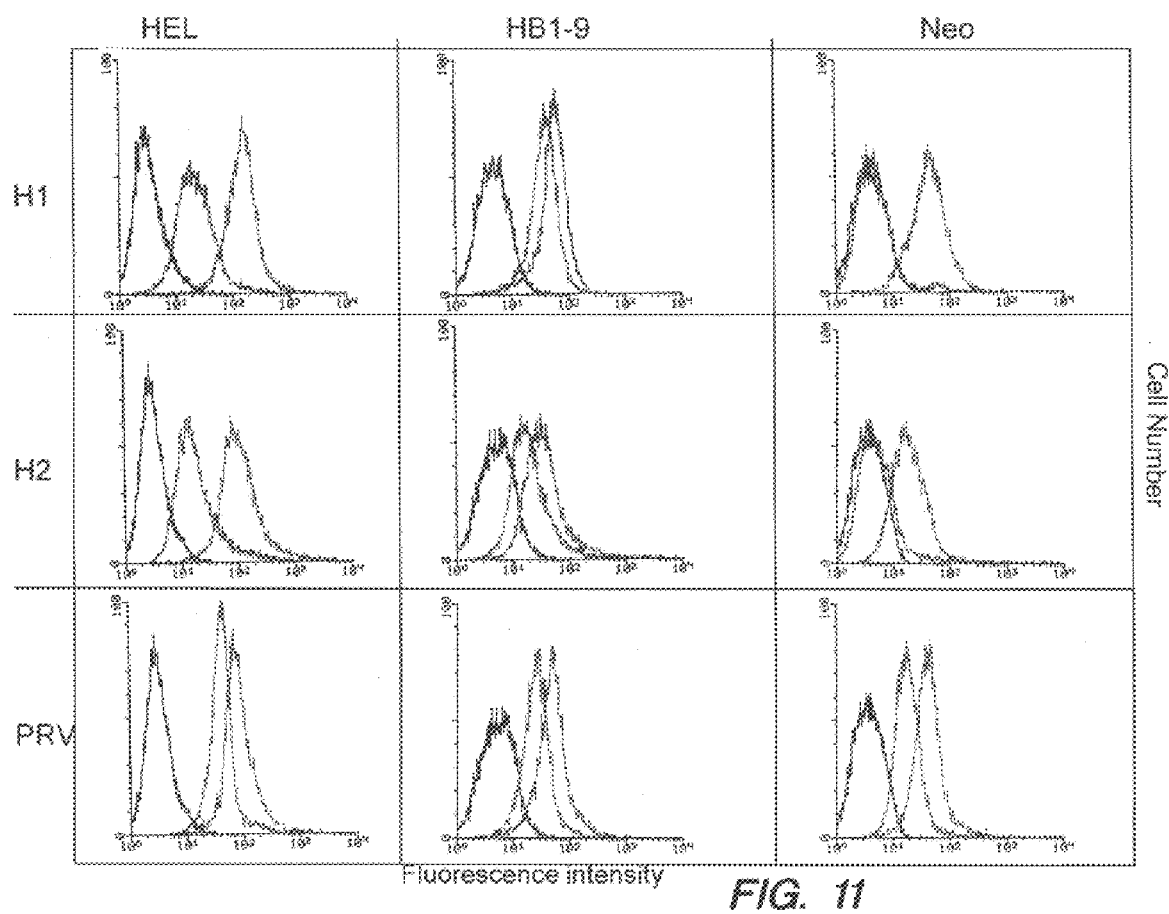
FIG. 11 shows binding of virus to porcine cells expressing HVEM by FACS analysis. [FIB1-9 (A7 cells expressing HVEM) and Neo (vector only A7 cells)].

Infection of HB 1-9 cells (HVEM expressed in porcine A7 cells) with three strains of HSV-1 and of HSV-2 (FIG. 10) showed that the virus enters, replicates and produces yields for each to levels equal to, or greater than, from Hep-2 cells. This entry was not strain or serotype specific, in contrast to CHO cells where HVEM increases HSV-1 blue foci (yields cannot be measured), but had less effect on HSV-2 CHO cells were not as defective in HSV-2 entry as HSV-1. Penetration of HSV into HB1-9 cells was rapid and the cells could not be saturated by the highest levels of UV-inactivated virus. FACS analysis (FIG. 11) showed that most virus that associated with HB1-9 cells was stably attached (heparin elution resistant). Stable attachment could not be detected on A7 cells in the absence of HVEM.

Figure 12A:
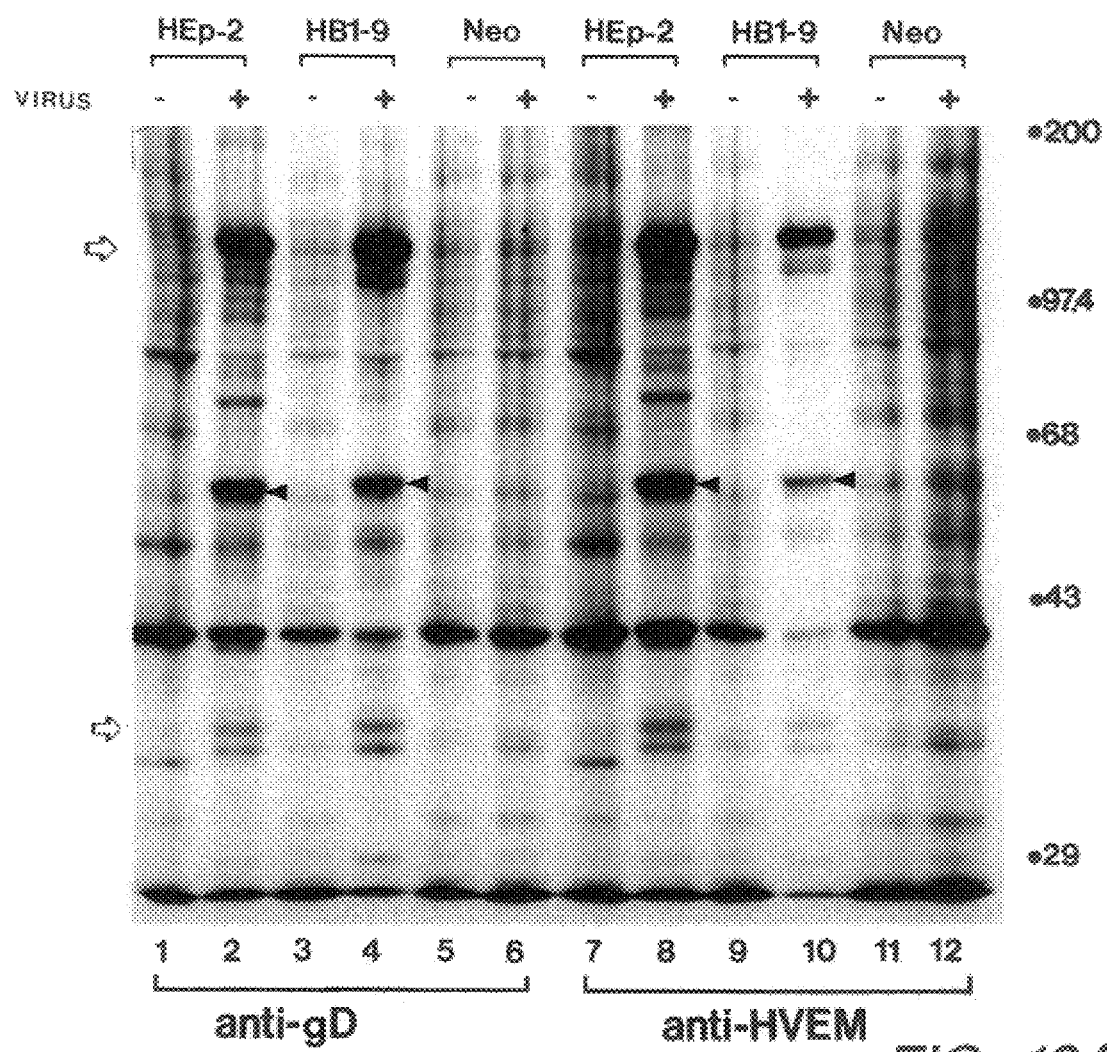
FIGS. 12A and 12B are gels which show interaction of HVEM with viral proteins by immuno-precipitation and Western blot analysis.
Figure 12B:
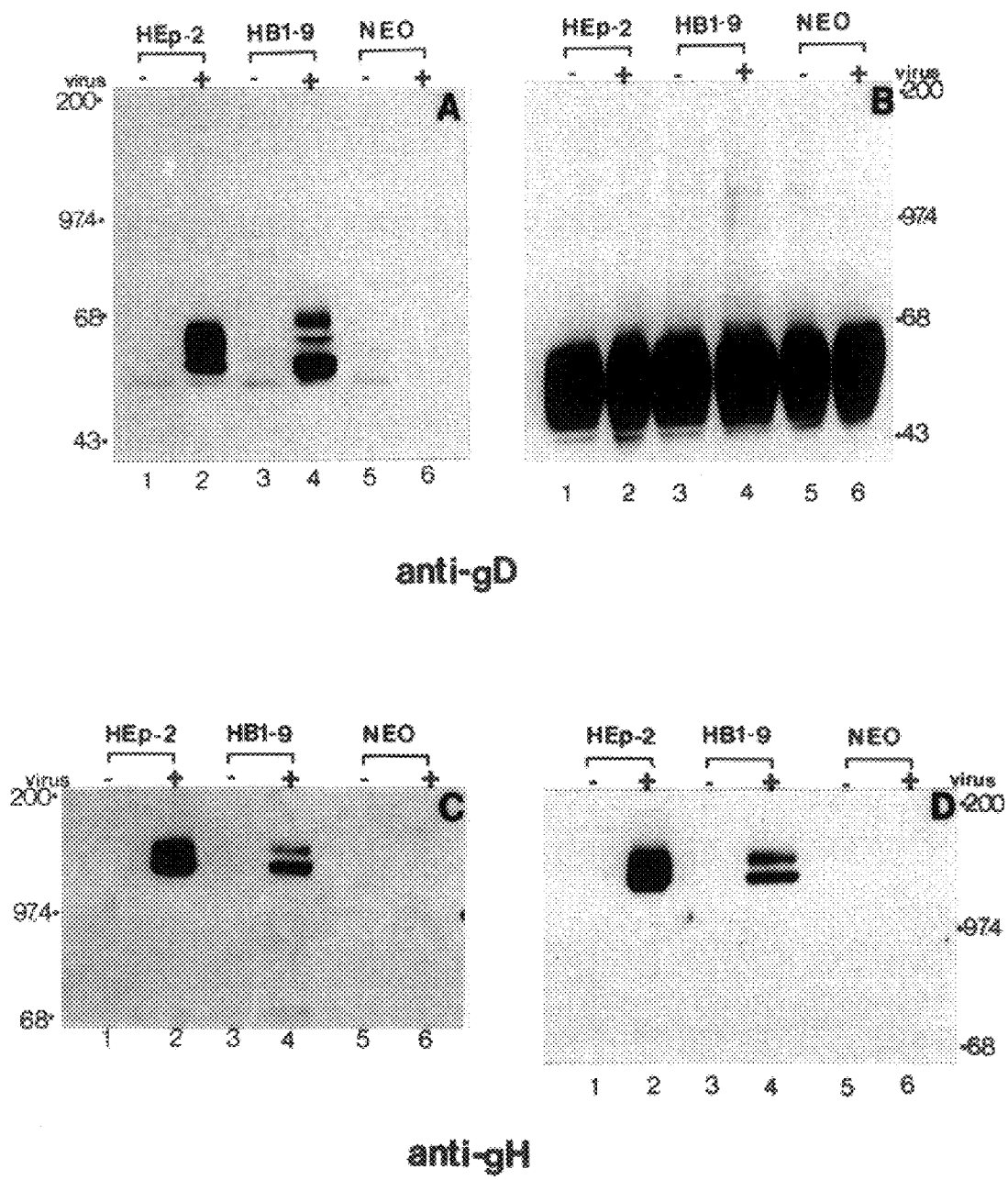

Immunoprecipitation with anti-gD and anti-HVEM antibody showed that gD and a band at the proposed molecular weight of HVEM (~35,000 kd) appeared when either antibody was used (FIG. 12A). In addition a band specific to infected cells appeared at approximately 110 kd. Western blots with anti-gH and anti-gD antibody showed that the band contained gH, but not gD multimers (FIG. 12B). These data indicated that HVEM, gD, gH and perhaps other cellular or viral proteins specifically interacted in some manner in susceptible Hep-2 and HB 1–9 cell but not in A7 or Neo cells. This agreed with the model prediction (FIG. 1) that when gD binds to mediate stable attachment to a non-HS cell receptor (or receptor complex), such binding may alter conformations of gH to reveal its potential fusogenic domains, or new receptor binding sites. gH is conserved among the herpesvirus family and is highly hydrophobic. It elicits potent neutralizing antibodies that block penetration, and is required for HSV entry. Therefore, gH has been postulated to function as an HSV glycoprotein that initiates membrane fusion. Transfection with viral DNA or infection of HB1-9 cells with syncytia mutants or wild-type HSV resulted in syncytia plaques or massive fusion of monolayers. This suggested that HB1-9 cells that express HVEM are more susceptible to viral induced fusion, and is likely if HVEM was one component of a receptor complex that facilitates virion-cell fusion during entry. A1 so, HSV plaques appeared when viral DNA is transfected to bypass entry. Thus, this example shows that HVEM or other human components required for HSV entry, are not required for HSV spread in cells. However, when present, HVEM mediates entry and enhances fusion.

What is claimed is:

1. A composition, comprising an isolated nucleic acid encoding the polypeptide having the amino acid sequence set forth in SEQ ID NO:2.

2. The composition of claim 1, wherein said nucleic acid comprises the sequence set forth in SEQ ID NO:1.

3. The composition of claim 1, wherein said nucleic acid is in a vector.

4. The composition of claim 3, wherein said vector is in a host cell.

5. The composition of claim 4, wherein said host cell is a non-human cell.

6. The composition of claim 5, wherein said host cell is a porcine cell.

7. The composition of claim 6, wherein said porcine cell line does not express an endogenous human herpes simplex virus receptor.

8. A composition, comprising a clonal porcine cell line which expresses a non-endogenous nucleic acid encoding the polypeptide having the amino acid sequence set forth in SEQ ID NO:2.

9. A method for testing compounds, comprising:

a) providing: i) human herpes simplex virus, ii) a first population of cells, said first population being non-permissive for human herpes simplex virus, iii) an isolated nucleic acid encoding the polypeptide having the amino acid sequence set forth in SEQ ID NO:2, and iv) a compound suspected of being capable of inhibiting human herpes simplex virus entry into cells;

b) transfecting said first population of cells with said nucleic acid under conditions so as to create a second population of cells being permissive for human herpes simplex virus;

c) mixing, in any order, said human herpes simplex virus, said compounds and said second population of cells; and d) measuring the extent of human herpes simplex virus entry to said cells.

10. The method of claim 9, wherein said first population of cells are non-human cells.

11. The method of claim 10, wherein said non-human cells are porcine cell.

12. The method of claim 9, wherein said compound is an antibody.

\* \* \* \* \*